United States Patent
De Franciscis et al.

(10) Patent No.: US 8,492,082 B2
(45) Date of Patent: Jul. 23, 2013

(54) METHOD FOR OBTAINING OLIGONUCLEOTIDE APTAMERS AND USES THEREOF

(75) Inventors: Vittorio De Franciscis, Naples (IT); Laura Cerchia, Naples (IT); Gerolama Condorelli, Naples (IT)

(73) Assignee: Consiglio Nazionale delle Richerche, Rome (IT)

( * ) Notice: Subject to any disclaimer, the term of this patent is extended or adjusted under 35 U.S.C. 154(b) by 0 days.

(21) Appl. No.: 13/061,373

(22) PCT Filed: Sep. 1, 2009

(86) PCT No.: PCT/EP2009/061276
§ 371 (c)(1),
(2), (4) Date: Feb. 28, 2011

(87) PCT Pub. No.: WO2010/023327
PCT Pub. Date: Mar. 4, 2010

(65) Prior Publication Data
US 2011/0166213 A1   Jul. 7, 2011

(30) Foreign Application Priority Data

Sep. 1, 2008   (EP) .................................. 08105194

(51) Int. Cl.
*C12Q 1/68* (2006.01)
*C12P 19/34* (2006.01)
*G01N 33/48* (2006.01)
*C07H 21/04* (2006.01)

(52) U.S. Cl.
USPC ................ 435/6; 435/91.2; 436/94; 536/24.5

(58) Field of Classification Search
None
See application file for complete search history.

(56) References Cited

FOREIGN PATENT DOCUMENTS

| WO | 2005/093097 A | 10/2005 |
|----|---------------|---------|
| WO | 2006/096754 A | 9/2006  |
| WO | 2008/019142 A | 2/2008  |

OTHER PUBLICATIONS

Pestourie C., et al., "Comparison of different strategies to select aptamers against a transmembrane protein target", Oligonucleotides, vol. 16, No. 4, 2006, pp. 323-335.
Cerchia L., et al., "Neutralizing aptamers from whole-cell SELEX inhibit the RET Receptor Tyrosine Kinase", PLOS Biology, vol. 3, No. 4, Apr. 2005, pp. 697-704.
Wang C., et al., "Single-stranded DNA aptamers that bind differentiated but not parental cells: subtractive systematic evolution of ligands by exponential enrichment", Journal of Biotechnology, Elsevier Science Publishers, Amsterdam, NL, vol. 102, No. 1, Apr. 10, 2003, pp. 15-22.
Blank M., et al., "Systematic evolution of a DNA aptamer binding to rat brain tumor microvessels", Journal of Biological Chemistry, American Society of Biolochemical Biologists, Birmingham, US, vol. 276, No. 19, May 11, 2001, pp. 16464-16468.

*Primary Examiner* — Amy Bowman
(74) *Attorney, Agent, or Firm* — Lucas & Mercanti, LLP

(57) ABSTRACT

The present invention relates to a method for obtaining nucleic acid aptamers that bind to cancer cell-surface epitopes, to the aptamers generated using this method and their use for therapeutic, diagnostic and prognostic purposes.

13 Claims, 19 Drawing Sheets

Figure 1:
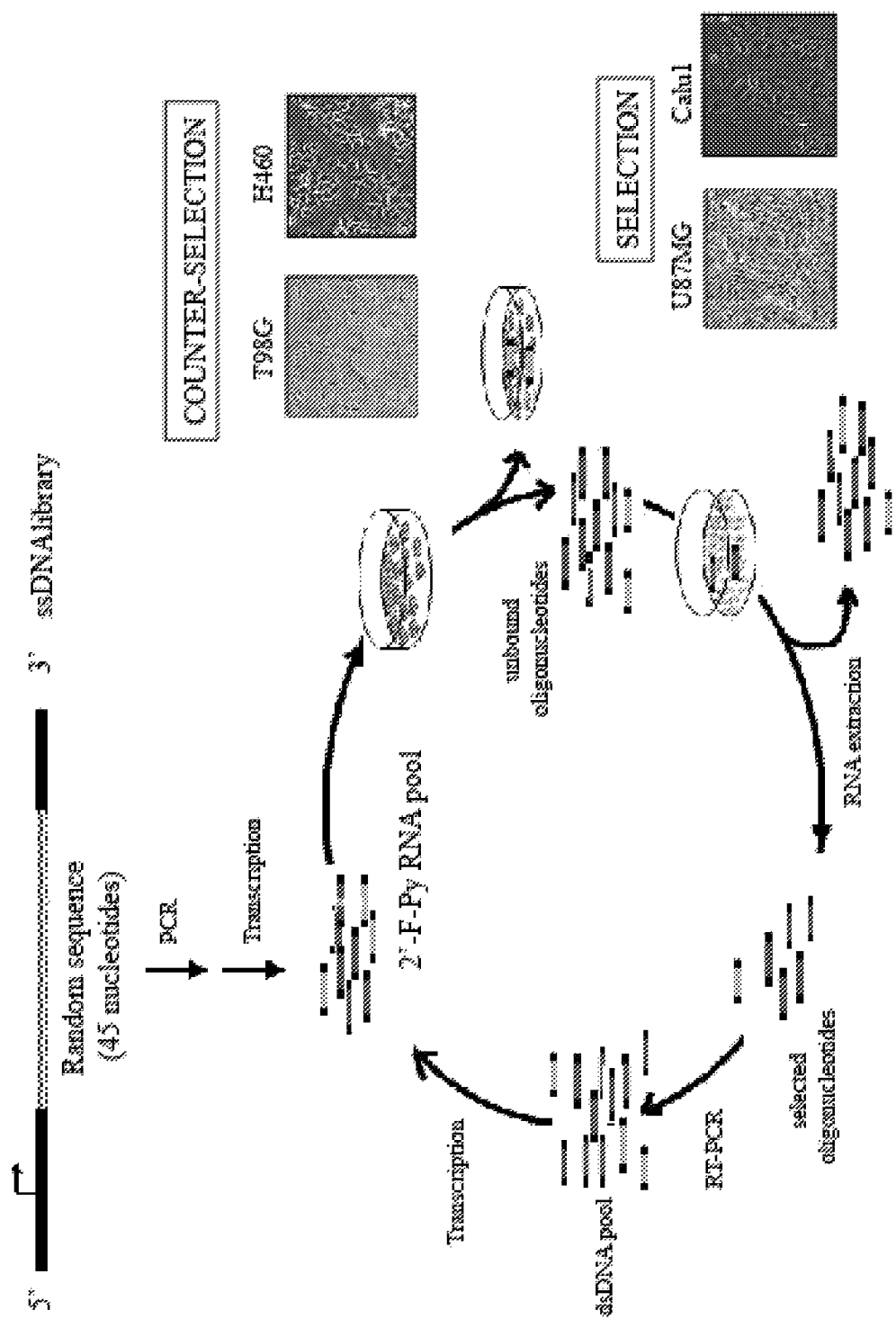

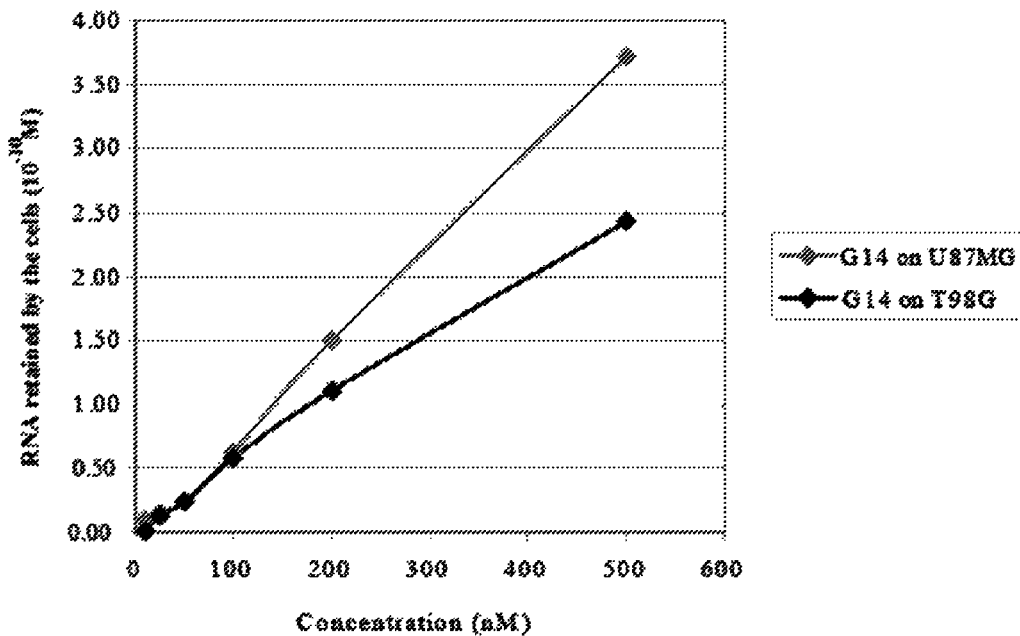
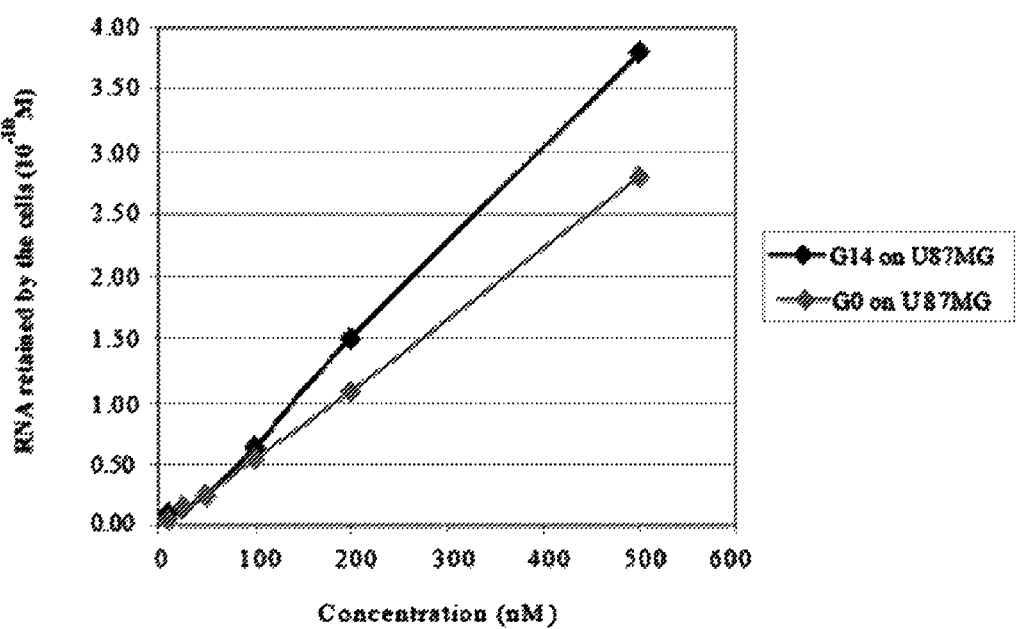
Fig 3

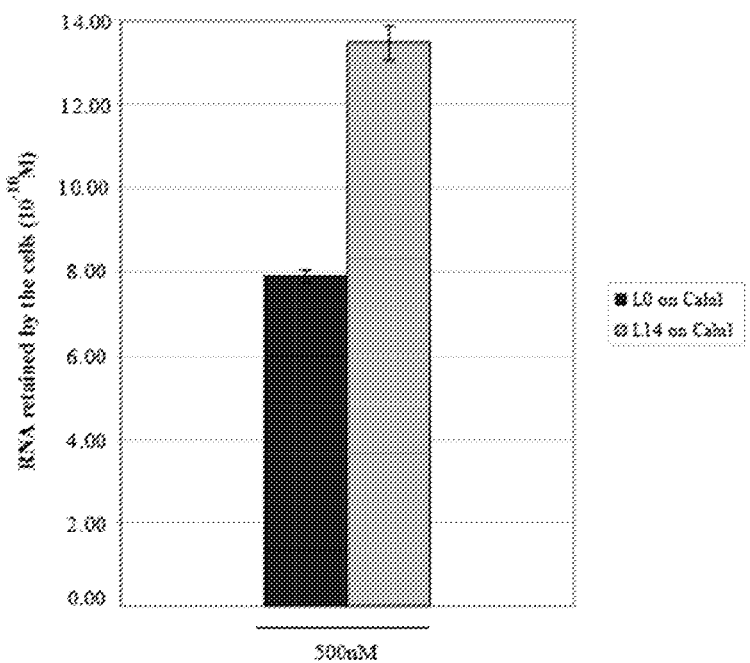
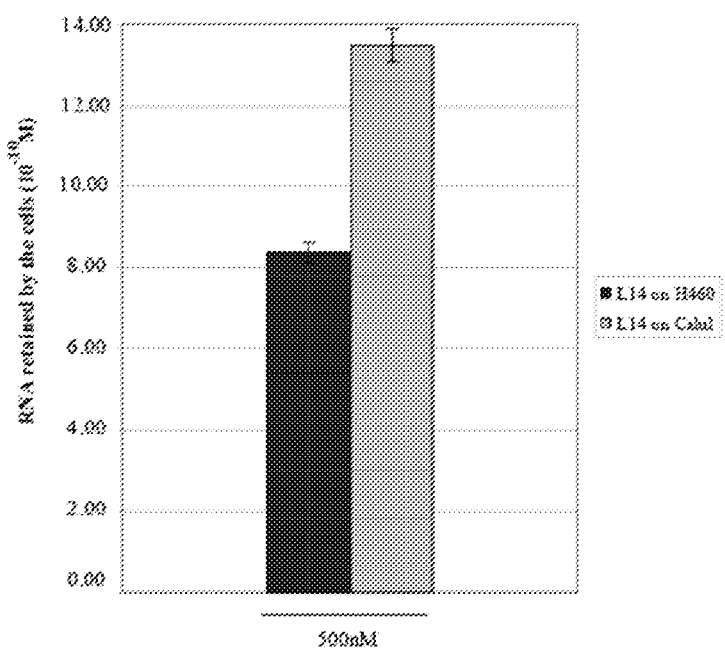
Fig 4

```
                            10        20        30        40        50        60
                    ....|....|....|....|....|....|....|....|....|....|....|....|.
          B28-     ----------TCGTTTACATTGTACTCTCCATTAATGACCCTCGGATTGCTTAG------------
          D7-      ---------ACTATCAATGCCTGACGCACGAT-AATCTTGCTGGTCTCACAGAA------------
          C4-      -----CCGCAATGACTACCGTCTTGCA-GTTTTTATAGCGTACTCTCAATG----------------
          C28-     ----------CTGTCGAGCTTCATTCATGTGCTCACCGCTTACGCCTAATGTCAT-----------
          A2A21-    ---------TTGCATTTACTCGATGTCCCACGACAA-TGTGATACCTCTTATGA-----------
          C15-     ----------TTGCATTTACTCGATGTCCCACGACAA-TGTGATACCTCTTATGA-----------
          C24-     ----------TTGCATTTACTCGATGTCCCACGACAA-TGTGATACCTCTTATAA-----------
          C8-      ----------TTGCATTTACTCGATGTCCCACGACAA-TGTGATACCCCCTCAA-----------
          D14-     ----CGAACGTTGTATTTACTTGACCTCGCACTA-----GTTTAGCTTCCTACA------------
          D6-      ----CGAACGTTGTATTTACCTGACCTCTCACTA-----GTTTAGCTTCCTACA------------
          B18-     ---------TGCACATGAGTATTTATTCATCTCAAACGCTGACCTGCCAATAA-------------
          A7-      --------CCGTTGT-TCTACATG-TCACTCATCATGCGAGTCTTTT-GTCTACA-----------
          B2-      --------CCGTTGT-TCTACATG-TCAGTCATCATGCGAGTCTTTT-GTCTACAA----------
          B19-     --------CCGTTGT-TCTACATG-TCACTCATCATGCGAGTCTTTTTGTCTA-------------
          A6B15-   --------CCGTTGT-TCTACATG-TCACTCATCACGCGAGTCTTTT-GTCTAA------------
          C2-      -TTGCCAATACAGTTGATCATTGTCTTACCATTGACTAGTACC-----------------------
          C10-     ---CCCAAGTCAGT-GATTGGTAACTTTCACTTGAC-AATATCAAATGCC----------------
          C1-      --------GCCTCTCAACGATTAATGTTTCATTAAC-ATGATCAATCGCCTCAA------------
          B22-     --------GCCTCTCAACGATTAATGTTTCGTTAAC-ATGATCAATCGCCTCAA------------
          C5-      -----------GGCATTTGATATTGTCAAGTGAAA-GTTACCAATCACTGAC--------------
          D23-     -TTATTAACGTTATCATTGTTCTTCACTACTTGTAGTACCTTCGA---------------------
          C22-     ---------CGTTATTACTATGTATCACAACGTGAACCCATGTTGAATCACAA-------------
          D2-      ---------------CCGTCZATCGCGAAGCGTCTACTATCCTTGTTC---AATTGTGACTTC----
          B13-     --------------------CTGCACAGCGTCCACACAACTTGATCCACAATTTTGATGCCTTAT
          B3-      ----------CA-ACGATGCTTGTTA-CGCGTAA-TCTTAGTCACATTGCTTGCGT----------
          C9-      ----------CA-ACGATGCTTGTTA-TGCGTAA-TCTTAGTCACATTGCTTGCGT----------
          A20-     ----------CACACGATTGTTATAAGCGCATTACTCTCGTCCCACTGTACTTGA-----------
          A2-      ---------TAACGTGCTATTCAGAACTTTGTCT-GCCCACTTTTAGTGAACTCCA----------
          D3-      --------------TCCATTTTGGATGATCGTTG--TGATTCTCGTAATACAAGCCTTCA------
          C16-     ----------CTATCAATAGTTGAC-ATCGTTCGCTGTCTATCGCAATACTATCC-----------
          C7-      -------------CTTCATGTTGATCGCTTATAAACTCACATAGTTAGTCTCATAA---------
          C12-     ---------TGAGTGTTATCGAGTTGATCGACAATACAATCTCACAAT-ACCTTC-----------
          D9-      ----TACCAAACGCGCGGTTTCG--TCTCGTAATAACCAAA---TGCCTCTGA-------------
          A9-      ----TACCAAACGCGCAATTTTCA--TCTTGTAATAACCAAA---TGCCTCTGA-------------
          D21-     --------CAGTCGCGAATTTTTTATTCTTTCTTACAACAAAGCATAGCCTCA-------------
          C18-     ---------GATTGCGGATTCTCA--TCTTTCAACAACGAA--CTAGCCTCTACTA-----------
          C23-     TTGTCAACGATCGAGCACGTTC----TCACACAA-AGCCTCTTACTAT-AT----------------
          C6-      --------CAATCGCGTACGTTC----TTGCGTAACAAACAGCCACTGTCATAAAC----------
          D13-     -----------CGTTTACGCGT-----AATCTTGTAATTCAC-ATTCTCTCAACAAGCCTA-----
          A4-      ----------GACATCAACATCTCA-ACGATCTTGTTACTCTC-A---ACTCAAATAGC-------
          A5-      ----------ACGTT-ACTCTT---GCAACAC--AAACTTTA-ATAGCCTCTTATAGTTC------
          A10C13-  ----------ACGTT-ACTCTT---GCAACACCCAAACTTTA-ATAGCCTCTTATAGTTC------
          D18-     ----------ACGTT-ACTCTT---GCAACACCCAAACTTTA-ATAGCCTCTTACAGAA-------
          D5-      -------------TACAGCGCTAT-TCTT--CCAACCAATCATACCACCTTGTCATGTTAA-----
          C14-     ----------CGAATCGAAGCGATAT-TCCTTACCAATTAATTGTATAGCCTTA-------------
          D19-     ----------TGTTGCAACATCGA-GTC-AGCGTGTTCTTCCAAGCCTCTATAGAAC----------
          D4-      ------CATCGAATACAGCCTTTA-ATCCAACCTCCAATTTCAATCGACTAA--------------
          B7-      -------------TTCAGCGATG---TTCTAATCACCACATAACAAACTATAGCCAGACCT-----
          B8-      --------------TGATCGTTGA-ATTCAACTGTCCACTTAACAAATTTCAGCCACTAA-----
          D22-     -----------------TTCG--TGTCAACTCAACCAACCAA-GCCTTCTGACGTACACTAAG-
          C3C11D10- -----------ACAGCAATGA-TCTCTACACACAACAAATGCCTTCACACTA--------------
          B17-     ---------TGCGCGAATTCTA-TCCGTATGCAATTCATGCATACATTCCAAC-TA--------
          B14-     -----TTAGAATTCTAATTTGATAATATTACTTGCCGCCTCCACGAACAC----------------
          A3A1B4B8C19D11- -------------TGATTTTGCAGCACTTCTTGTTATCTTAACGAACTGTTGATGA----
          B16-     --------CTAAGAGGTTGACGCT-TAGCACTTCCAGTAACCTAAGCCTTCTA------------
          B4-      -------TGTTTGACTTGATT-CTCTAGCTTACA--AATGTTAACATCTGCAAA-----------
          D12-     --------TGTCTTGTTTATTCGAACTCACATTAACAACAATGATTAGACGGC-----------
          C21-     ----------CCGCAACAAGATT--GACGGCTTGCGTAAATTCACAAGATTTCATT
          B15-     ---------CTGTGACGACAGTTAAGATCGTATTCTGCCACCATACCTGTTGTA-----------
          D1D20-   --------TTCACACACTCAATTGAACGGTGATTCAAGTTATTAGCAGCCTCA------------
```

Fig 5

Fig 7

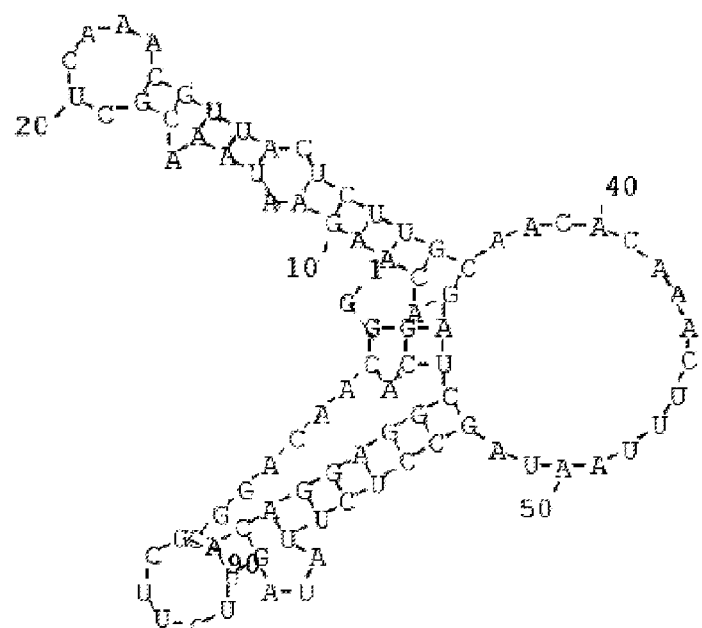
A5
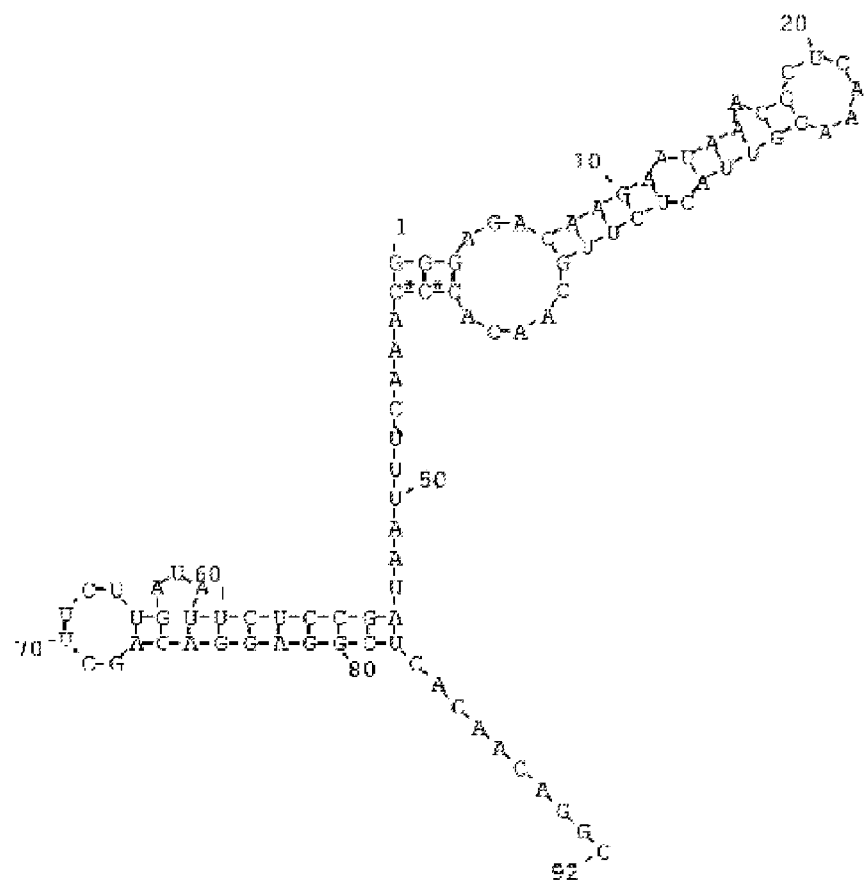
C13
Fig 10

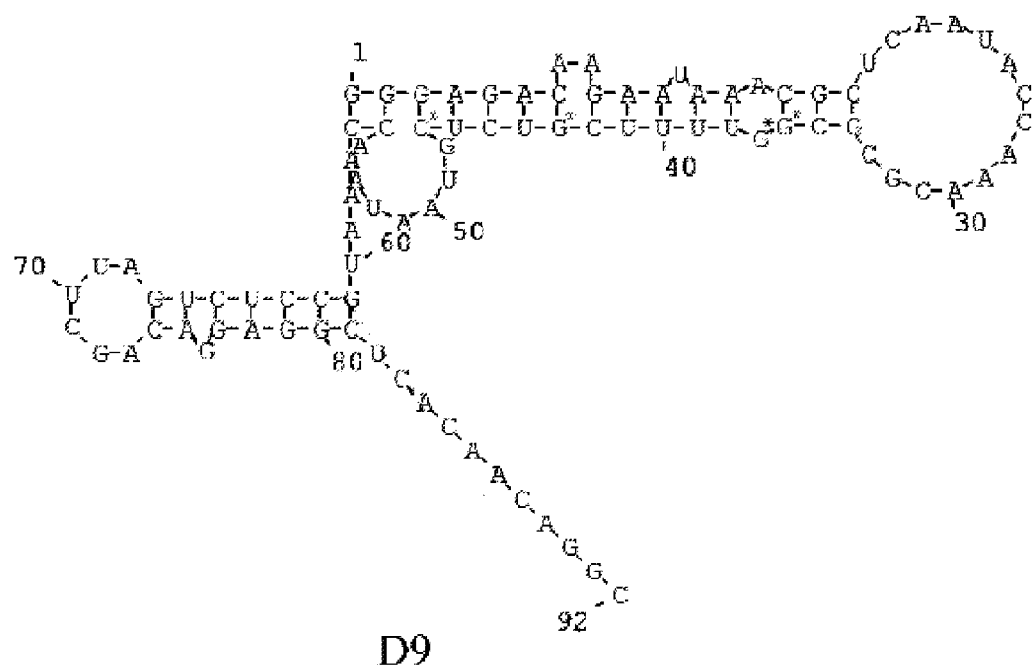
D9
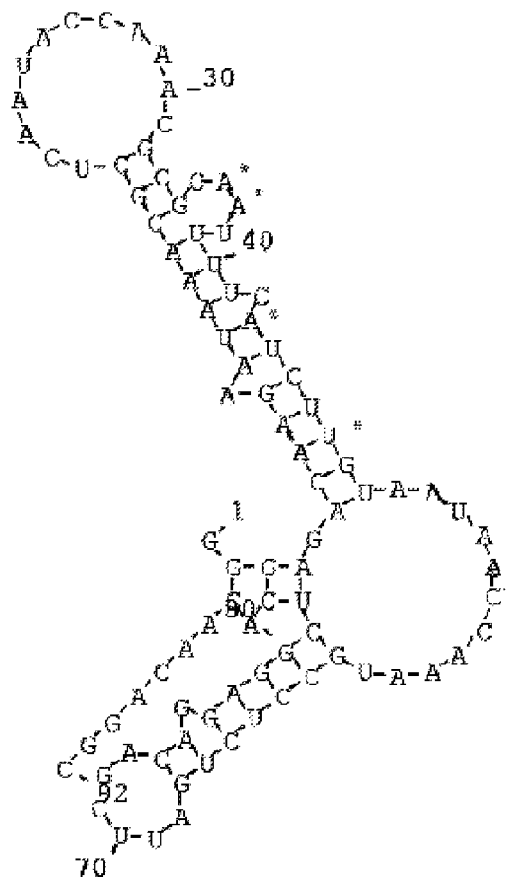
A9
Fig 10

A
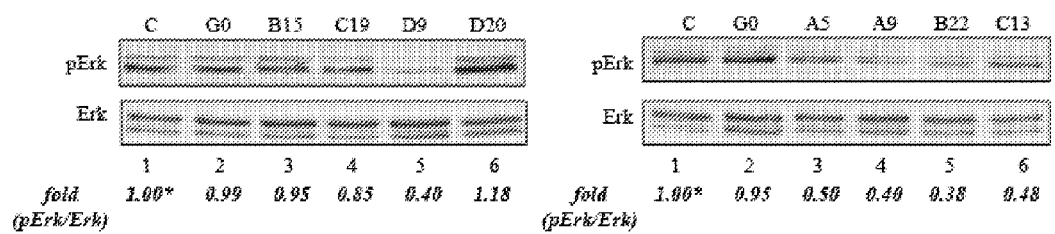
B
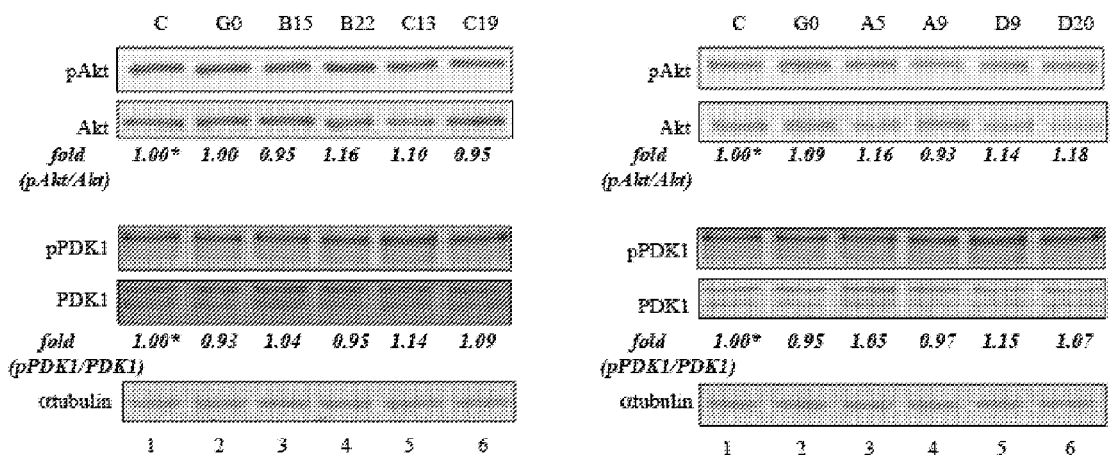
Fig 12

A
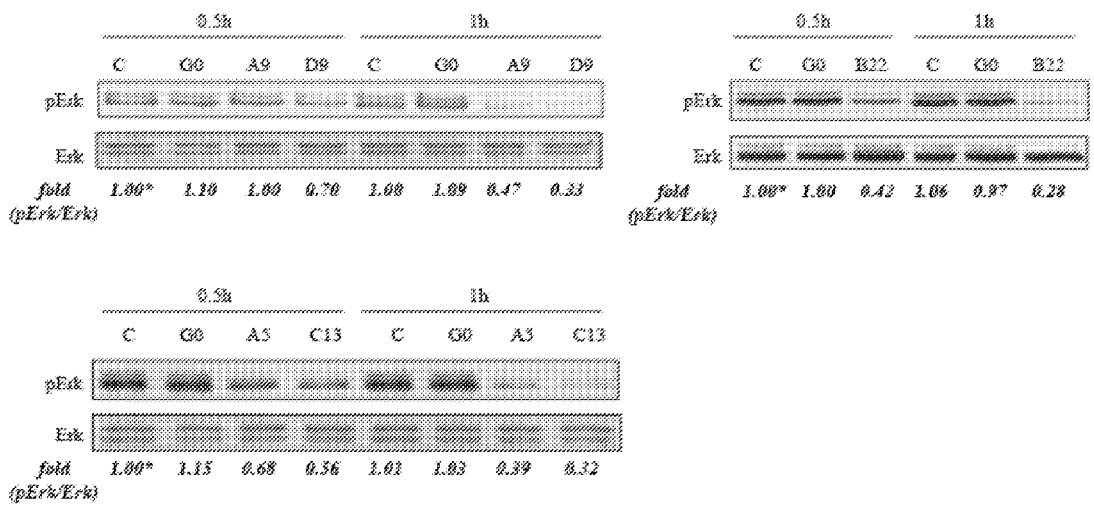
B
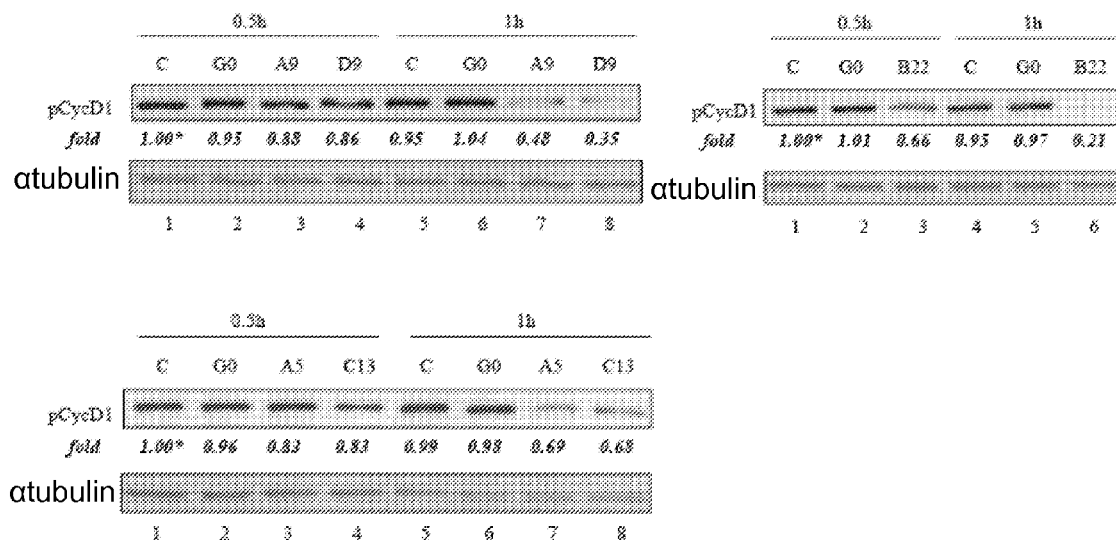
Fig 13

A
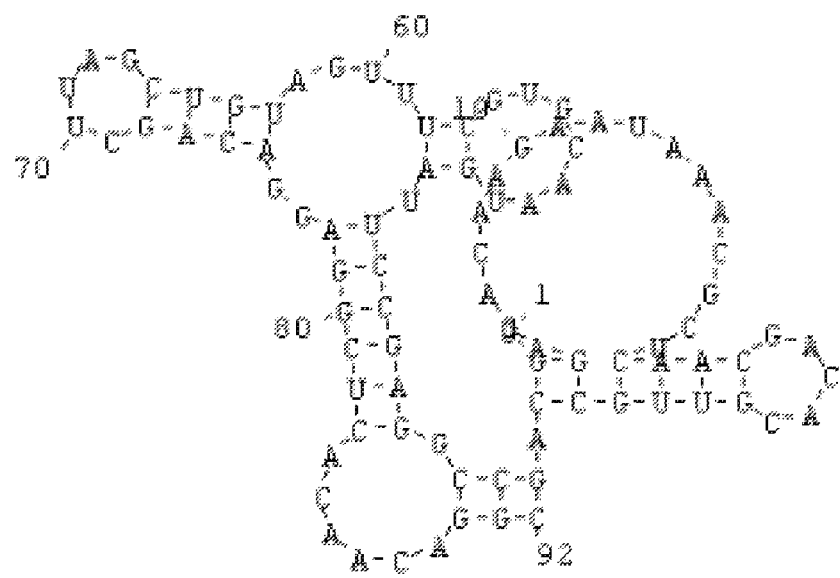
B
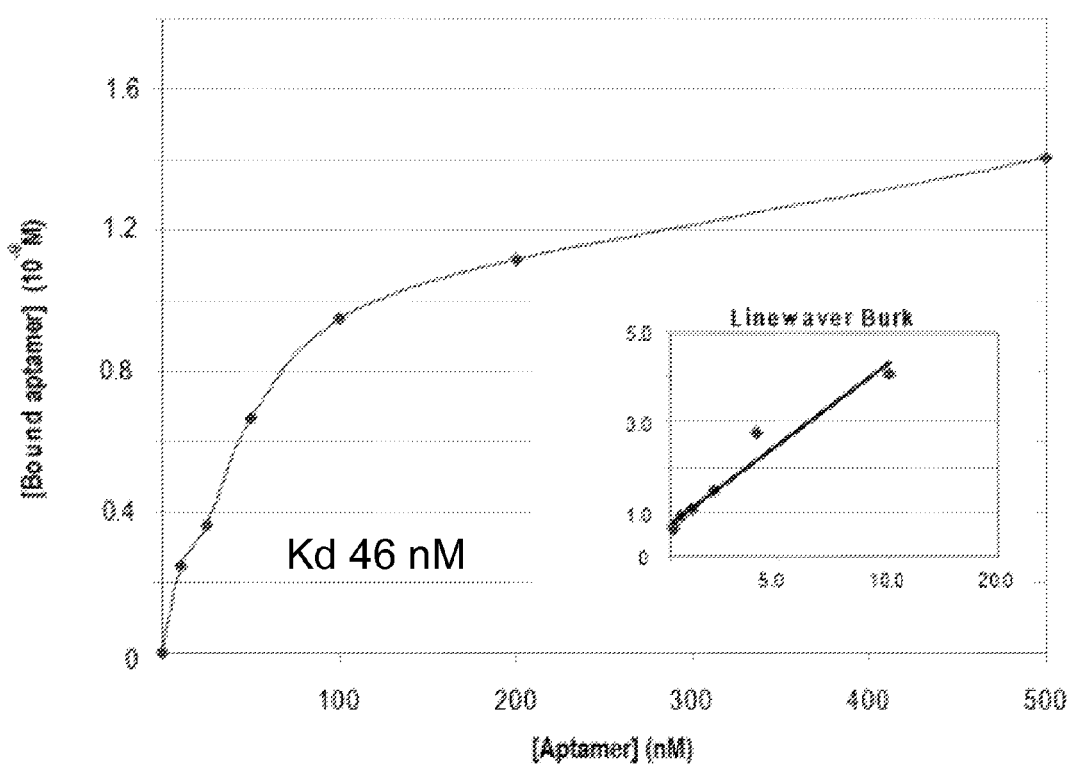
Fig 14 c

METHOD FOR OBTAINING OLIGONUCLEOTIDE APTAMERS AND USES THEREOF

CROSS-REFERENCE TO RELATED APPLICATIONS

This application is a 371 of PCT/EP2009/061276 filed on Sep. 1, 2009, which claims the benefit of European Patent Application No. 08105194.8 filed on Sep. 1, 2008, the contents of each of which are incorporated herein by reference.

FIELD OF THE INVENTION

The present invention relates to a method for obtaining nucleic acid aptamers that bind to cancer cell-surface epitopes, to the aptamers generated using this method and their use for diagnostic, prognostic and therapeutic purposes, including drug delivery.

BACKGROUND OF THE INVENTION

The hope of success of therapeutic interventions in cancer largely relies on the possibility to distinguish, with high accuracy, even closely-related tumor types. Indeed, the identification of tumor specific signatures has been a major challenge of the last ten years to predict the responsiveness to a given therapeutic plan and to reduce the impact of side effects to be expected if unresponsive oncologic patients are being treated.

The SELEX technique refers to Systematic Evolution of Ligands by EXponential enrichment. Single-stranded oligonucleotides have the diversity characteristic both in molecular structure and function, thus, a random library of single oligonucleotides is synthesized for binding to a target protein on the membrane. The oligonucleotides bound non-specifically are washed away and the oligonucleotides bound specifically were eluted in denatured condition and collected. The oligonucleotides are amplified by PCR for further selection. The high affinity oligonucleotides, namely aptamers that have high affinity with the target proteins, can be selected from the initial library through amplification and selection over many cycles. In 1990, Tuerk and Gold selected Aptamers of T4 RNA polymerase by SELEX (Tuerk C and Gold L. 1990). Subsequently, Ellington and Szostak showed great interests in the application of aptamers in scientific research and production. Aptamers soon become a valuable research tool and show great application prospected in the fundamental research, drug selection and clinical diagnosis and therapy (Ellington and Szostak, 1990). At present, many kinds of aptamers have come into clinical test phase. For example, drugs for curing thrombus and inhibiting endometrium hyperplasic and angiogenesis (Green L S et al., 1995, Tasset D M, et al., 1997, Ruckman J et al., 1998).

An innovative aspect of the aptamers is their use in "target identification/validation" to identify various cell surface targets of a specific cellular state.

The U.S. Pat. No. 5,580,737 discloses a method for identifying nucleic acid ligands to a target molecule comprising contacting a mixture of nucleic acid with the target molecule, allowing the partitioning of increased affinity nucleic acid and then, contacting the increased affinity nucleic acid with non-target molecule. In particular ligand to theophylline and caffeine are described.

The patent application WO 2007/142713 provides a method for obtaining a probe specific for extracellular or cell-surface markers comprising several cycles of positive selection steps on a target cell followed by a step of counter-selection on a control cell. This method allows the selection of only a limited number of aptamers and only further to a high number of selection and/or counter-selection cycles. In addition, the selected aptamers display low cell specificity and are able to discriminate between cells of distant tumor types only (T-cell versus B cell lymphoma or small lung cancer cell versus large cell lung cancer, two cancer types of different origin).

Therefore, there is the need to provide a simplified method for obtaining aptamers comprising fewer cycles and resulting in aptamers with high specificity, even able to discriminate between different cells of the same tumor type, possessing different phenotypes (different resistance to a given physical or chemical therapeutic drug, different tumor mass growth properties, different ability to metastasize and different malignancy).

The authors of the present invention have already generated specific aptamers for the human receptor tyrosine kinase, Ret (Cerchia et al., 2005; WO 2005/093097), however they cannot be used to solve the problem of the invention.

The present invention discloses a simplified method to generate nucleic acid-based aptamers that bind to cancer cell-surface epitopes as unique tools to identify a surface molecular signature of cancer cells and thus permits to generate a small panel of high specific ligands capable of distinguish between even two closely related cell types. This approach, based on the use of living cells as target for the aptamers selection (whole-cell SELEX), allows selecting aptamers in a physiological context, and, most importantly, can be done without prior knowledge of the target molecules. The methods include much fewer steps than prior art methods. In addition and by contrast to the method of the application WO 2008/019142, the present protocol is specifically designed to target epitopes that are not internalised in the cell: ie short time of incubation of the library with cells are used and no trypsin treatment is performed. The present approach permits to identify and validate new tumor biomarkers.

The nucleic acid-based aptamers of the invention are able to discriminate between malignant and non malignant cell phenotype. The aptamers can also discriminate two different phenotypes within the same tumor cell type as for example, the resistance to a given physical or chemical therapeutic drug, the growth properties of the tumor mass, the ability to metastasize and the malignancy. The panel of aptamer molecules obtained and obtainable with the method of the present invention represent an innovative tool to detect cell surface specific epitopes as a signature of cancer cells in terms of tumor type, malignancy, therapeutic response, metastatic potential, proliferation and apoptotic rate. The panel of aptamer molecules obtained and obtainable with the method of the present invention represent an innovative tool to specifically target cancer cell with given surface specific epitopes in terms of tumor type, malignancy, therapeutic response, metastatic potential, proliferation and apoptotic rate.

SUMMARY OF INVENTION

Two types of human solid tumors were used as model systems, malignant glioma and non small cell lung carcinoma (NSCLC). Cultured human cancer cells that have close genetic background and only differ for their malignancy and/or therapeutic response were used as targets of the SELEX procedure. By coupling the Differential SELEX protocol to cancer cell lines, the authors were able to isolate different aptamers that are specific for targets present on the tumor cell type used (case 1: glioma; case 2: NSCLC) and absent on any other cancer type tested. Further, the authors of the present invention demonstrate that a small subset of aptamers is sufficient to distinguish two different cell lines of the same tumor type, but with different growth and therapeutic sensitivity (case 1 tumorigenic versus non-tumorigenic; case 2: TRAIL resistance versus sensitivity). Further, some of the aptamers have biological activity on the target cells.

Therefore it is an object of the present invention a method for selecting a nucleic acid aptamer specific for a protein selectively expressed on the cell surface of target cells comprising the steps of:
a) incubating a collection of synthetic nucleic acid oligomers with control cells, allowing oligomers to bind to them;
b) recovering a first set of unbound nucleic acid oligomers;
c) incubating the first set of unbound nucleic acid oligomers with target cells, allowing the first set of unbound nucleic acid oligomers to bind to them;
d) recovering nucleic acid oligomers bound to target cells;
e) amplifying and sequencing the nucleic acid oligomers bound to target cells.

Preferably, the first set of unbound nucleic acid oligomers recovered in step b) is incubated with the control cells and a second set of unbound nucleic acid oligomers recovered in step b) is further processed as indicated in steps c), d) and e).

Still preferably, the collection of synthetic nucleic acid oligomers is a synthetic library.

More preferably, the synthetic nucleic acid oligomers are labelled. Yet preferably the nucleic acid oligomers are oligoribonucleotides or modified RNA-se resistant oligoribonucleotides.

In a particular embodiment the target cell is a tumor cell and the control cell is a tumor cell of the same cell type as the target cell but having a different phenotype. Preferably, the tumor cell is a glioma cell or a NSCLC cell.

Still preferably, the phenotype is selected from the group of: resistance to a given physical or chemical therapeutic drug, tumor mass growth properties, apoptosis, ability to metastasize or malignancy, drug treated tumor cell.

It is a further object of the invention a nucleic acid aptamer obtainable according to the method of the invention. Preferably, the nucleic acid aptamer is for medical use. More preferably the nucleic acid aptamer is for the treatment of a tumor, also as targeting component for biocomplexes with nano particles or siRNAs. Still preferably the nucleic acid aptamer is for the diagnosis of a tumor and/or the follow-up of a therapy, also for molecular imaging. More preferably the nucleic acid aptamer is for predicting a therapeutic response of a drug for a tumor.

Preferably the tumor is a glioma or a NSCLC.

Still preferably, the nucleic acid aptamer is for the detection of a target cell.

Preferably, the target cell is a tumor cell. More preferably, the tumor cell is a glioma cell or a NSCLC cell.

More preferably, the nucleic acid aptamer has a sequence selected from the group of: SEQ ID No. 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129 or a functional fragment thereof.

Figure 16:
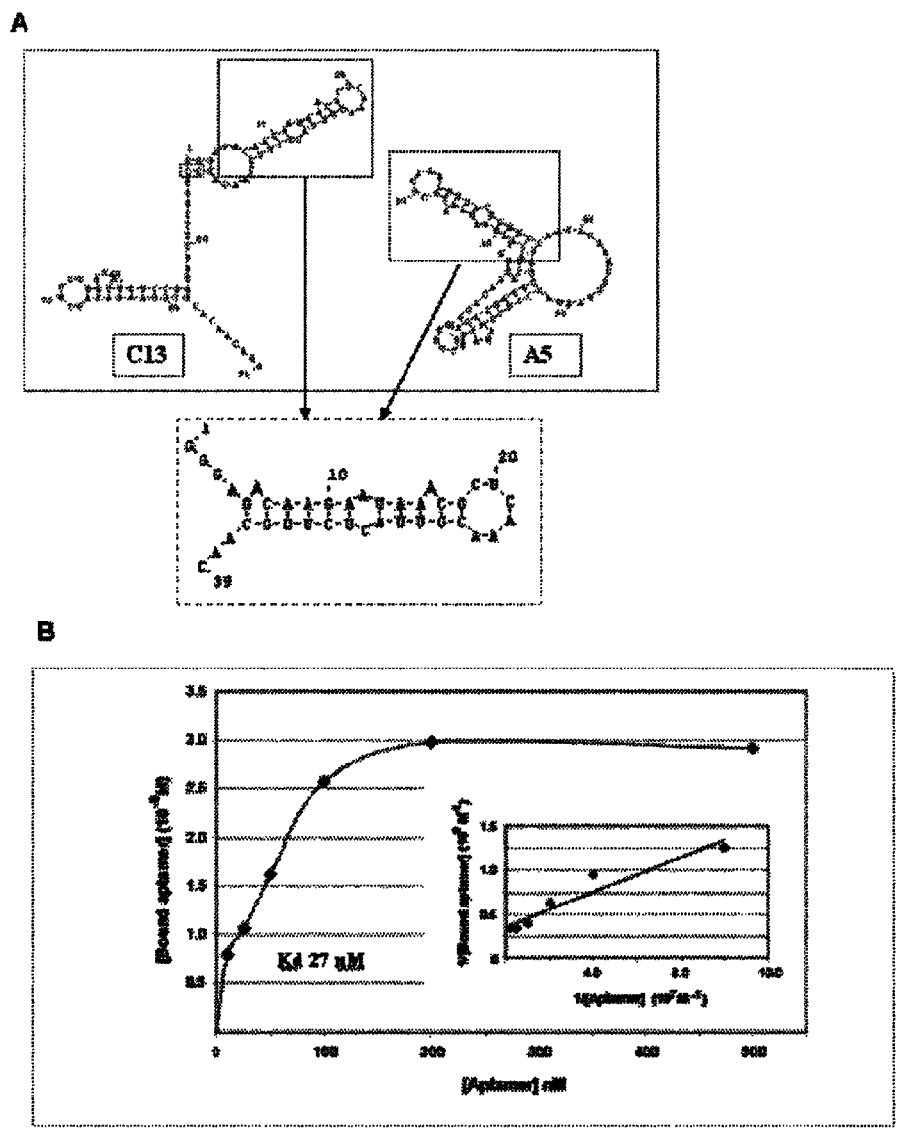
Figure 16:
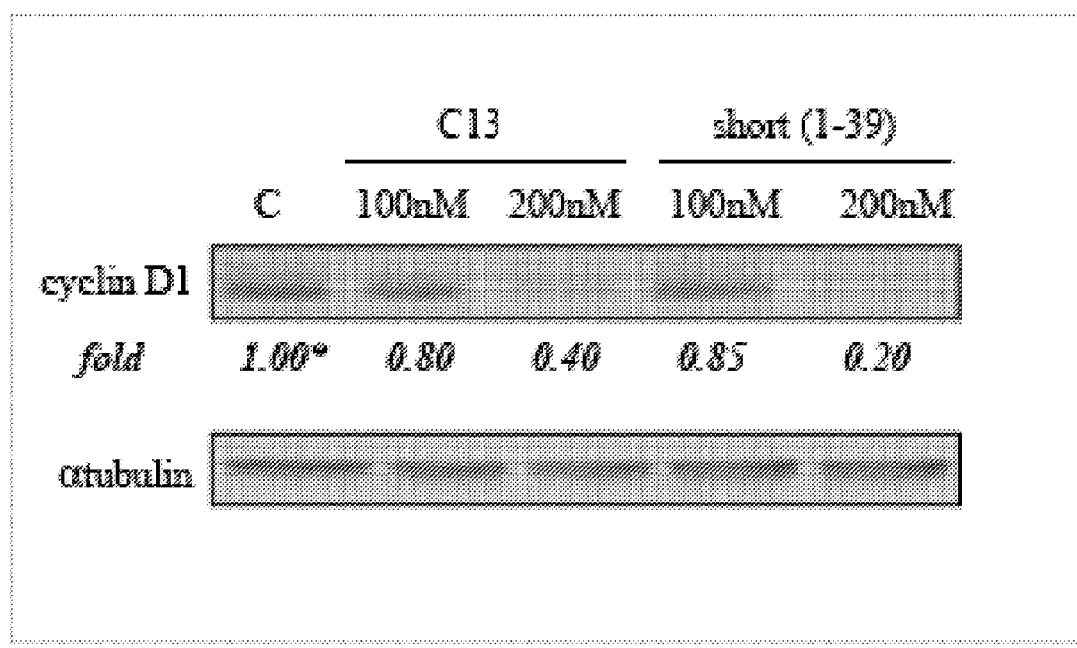

In the present invention, a functional fragment is meant as a fragment retaining essentially the same binding activity to the respective target as the sequence it derives from. The same binding activity means a binding with a Kd of 200 nM or less (see for example aptamers C13 and A5 and the common shorter sequence fragment C13 sh as indicated in FIG. 16).

It is a further object of the invention a pharmaceutical composition comprising at least one nucleic acid aptamer of the invention and suitable excipients and/or diluents and/or carrier.

The present invention shall be disclosed in detail in the following description also by means of non limiting examples referring to the following figures.

FIG. 1. Schematic Protocol for the Selection of cancer cell-specific aptamers. A pool of 2'F-Py RNAs was incubated with poorly tumorigenic T98G cells (Counterselection). Unbound sequences in the supernatant were recovered and incubated with tumorigenic U87MG cells for the selection step (Selection). Unbound sequences were discarded by several washings and bound sequences were recovered by total RNA extraction. Sequences enriched by the selection step were amplified by RT-PCR and in vitro transcription before a new cycle of selection. The same protocol has been used in the second example using the NSCLC cell line A459, for selection and the cells H460 for counterselection.

Figure 2:
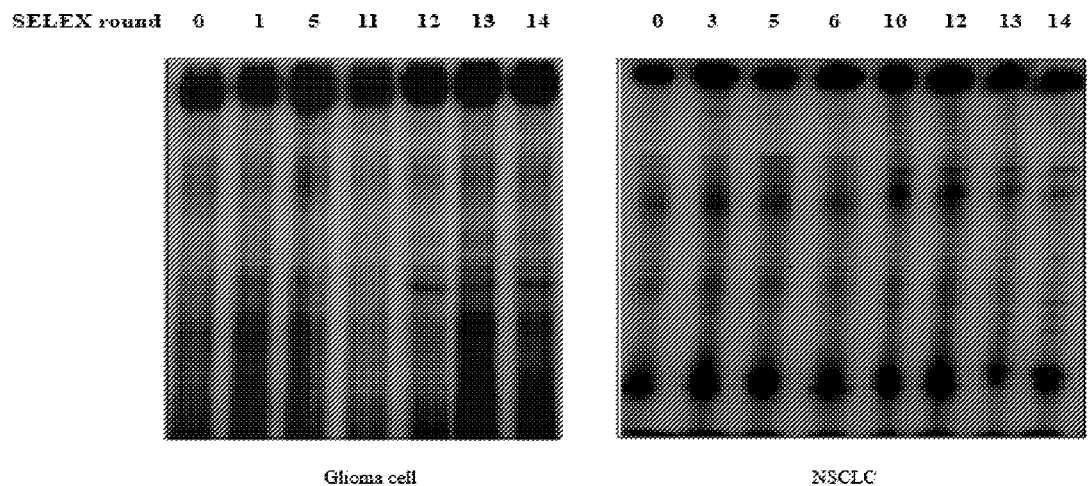

FIG. 2. Evolution monitoring of the whole-living cells SELEX. (A) Increase in the selection stringency during the SELEX protocol against Glioma (upper panel) and NSCLC (lower panel). (B) Estimation of the pool complexity during each round of SELEX by RFLP. [$^{32}$P] 5'-end-labeled double-stranded DNAs corresponding to the population of candidates from each of the indicated rounds (starting pool is indicated as 0, rounds analysed are: 1, 5, 11, 12, 13 and 14 for the selection on glioma, left panel, and 3, 5, 6, 10, 12, 13 and 14 for the selection on NSCLC, right panel) were digested with a combination of RsaI, AluI, HaeIII, HhaI endonucleases and analyzed by electrophoresis on a 6% denaturing polyacrylamide gel. Enrichment of the nucleic acid pools is assessed as the enrichment of specific digestion fragments within the random population that are visualised as bands in lanes 12, 13, 14 (glioma) and lanes 10, 12, 13, 14 (NSCLC).

FIG. 3. Binding analyses of the pool after 14 rounds of selection on glioma cells. The pool after 14 rounds of selection (named G14) or the starting pool (named G0) were 5'-[$^{32}$P]-labeled and incubated at increasing concentrations on the indicated cell lines.

FIG. 4. Binding analyses of the pool after 14 rounds of selection on NSCLC. The pool after 14 rounds of selection (named L14) or the starting pool (named L0) were 5'-[$^{32}$P]-labeled and incubated at 500 nM on the indicated cell lines.

FIG. 5. Alignment of sequences obtained from Whole-cell SELEX on glioma. 71 sequences (codified as B14, B10, C16, C23, etc.) obtained from the selection were aligned and analyzed using the BIOEdit sequence software. Out of 71 sequences obtained, 60 sequences are different. The sequences are reported as DNA and for simplicity, fixed-primer sequence at 5' and 3' extremities are removed.

| The sequence identifiers for sequences aligned in FIG. 5 are as follows, starting with B20: | |
|---|---|
| | SEQ ID NO: |
| B20 | 3 (codons 24-67) |
| D7 | 4 (codons 24-67) |
| C4 | 5 (codons 24-68) |
| C20 | 6 (codons 24-68) |
| A2A21 | 7 (codons 24-67) |
| C15 | 8 (codons 24-67) |
| C24 | 9 (codons 24-67) |

-continued

| The sequence identifiers for sequences aligned in FIG. 5 are as follows, starting with B20: | |
|---|---|
| | SEQ ID NO: |
| C8 | 10 (codons 24-66) |
| D14 | 11 (codons 24-68) |
| D6 | 12 (codons 24-68) |
| B10 | 13 (codons 24-67) |
| A7 | 14 (codons 24-67) |
| B2 | 15 (codons 24-68) |
| B19 | 16 (codons 24-66) |
| A6B15 | 17 (codons 24-66) |
| C2 | 18 (codons 24-65) |
| C10 | 19 (codons 24-68) |
| C1 | 20 (codons 24-68) |
| B22 | 21 (codons 24-68) |
| C5 | 22 (codons 24-63) |
| D23 | 23 (codons 24-67) |
| C22 | 24 (codons 24-67) |
| D2 | 25 (codons 24-68) |
| B13 | 26 (codons 24-68) |
| B3 | 27 (codons 24-66) |
| C9 | 28 (codons 24-66) |
| A20 | 29 (codons 24-69) |
| A2 | 30 (codons 24-69) |
| D3 | 31 (codons 24-67) |
| C16 | 32 (codons 24-67) |
| C7 | 33 (codons 24-66) |
| C12 | 34 (codons 24-68) |
| D9 | 35 (codons 24-68) |
| A9 | 36 (codons 24-68) |
| D21 | 37 (codons 24-68) |
| C18 | 38 (codons 24-67) |
| C23 | 39 (codons 24-68) |
| C6 | 40 (codons 24-67) |
| D13 | 41 (codons 24-67) |
| A4 | 42 (codons 24-67) |
| A5 | 43 (codons 24-66) |
| A10C13 | 44 (codons 24-68) |
| D18 | 45 (codons 24-67) |
| D5 | 46 (codons 24-68) |
| C14 | 47 (codons 24-66) |
| D19 | 48 (codons 24-68) |
| D4 | 49 (codons 24-68) |
| B7 | 50 (codons 24-68) |
| B8 | 51 (codons 24-68) |
| D22 | 52 (codons 24-66) |
| C3C11D10 | 53 (codons 24-68) |
| B17 | 54 (codons 24-68) |
| B14 | 55 (codons 24-68) |
| A3A1B4B8C19D11 | 56 (codons 24-66) |
| B16 | 57 (codons 24-67) |
| B4 | 58 (codons 24-67) |
| D12 | 59 (codons 24-68) |
| C21 | 60 (codons 24-67) |
| D15 | 61 (codons 24-68) |
| D1D20 | 62 (codons 24-68) |

Figure 6:
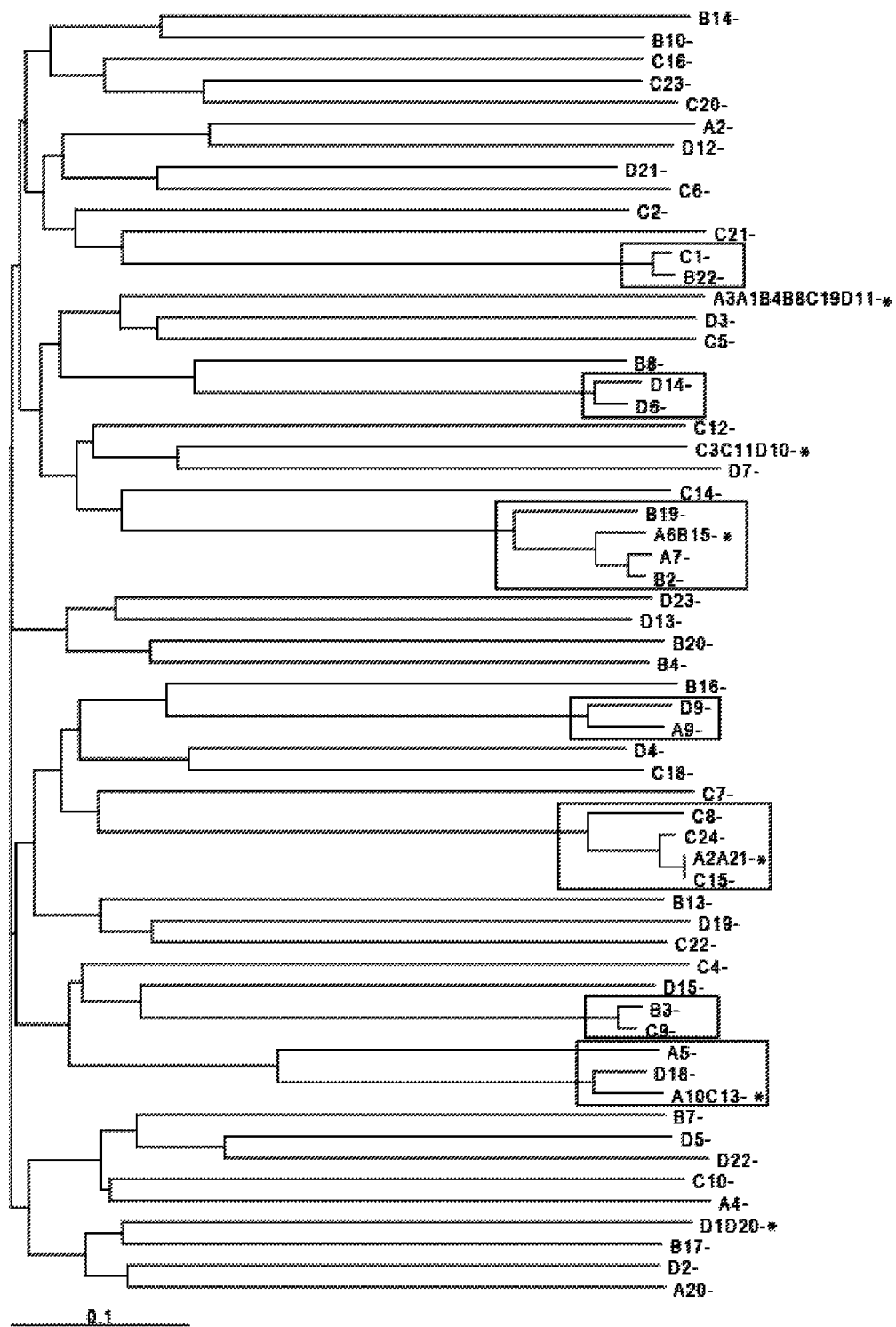

FIG. 6. Analysis of individual sequences similarity. Dendogram (obtained by using DNASIS software version 2.1) for visual classification of similarity among 71 individual sequences cloned after 14 rounds of selection. Aptamers that share sequence similarity are grouped in families (boxed); sequences found more than once are labeled with the asterisk.

Figure 7:
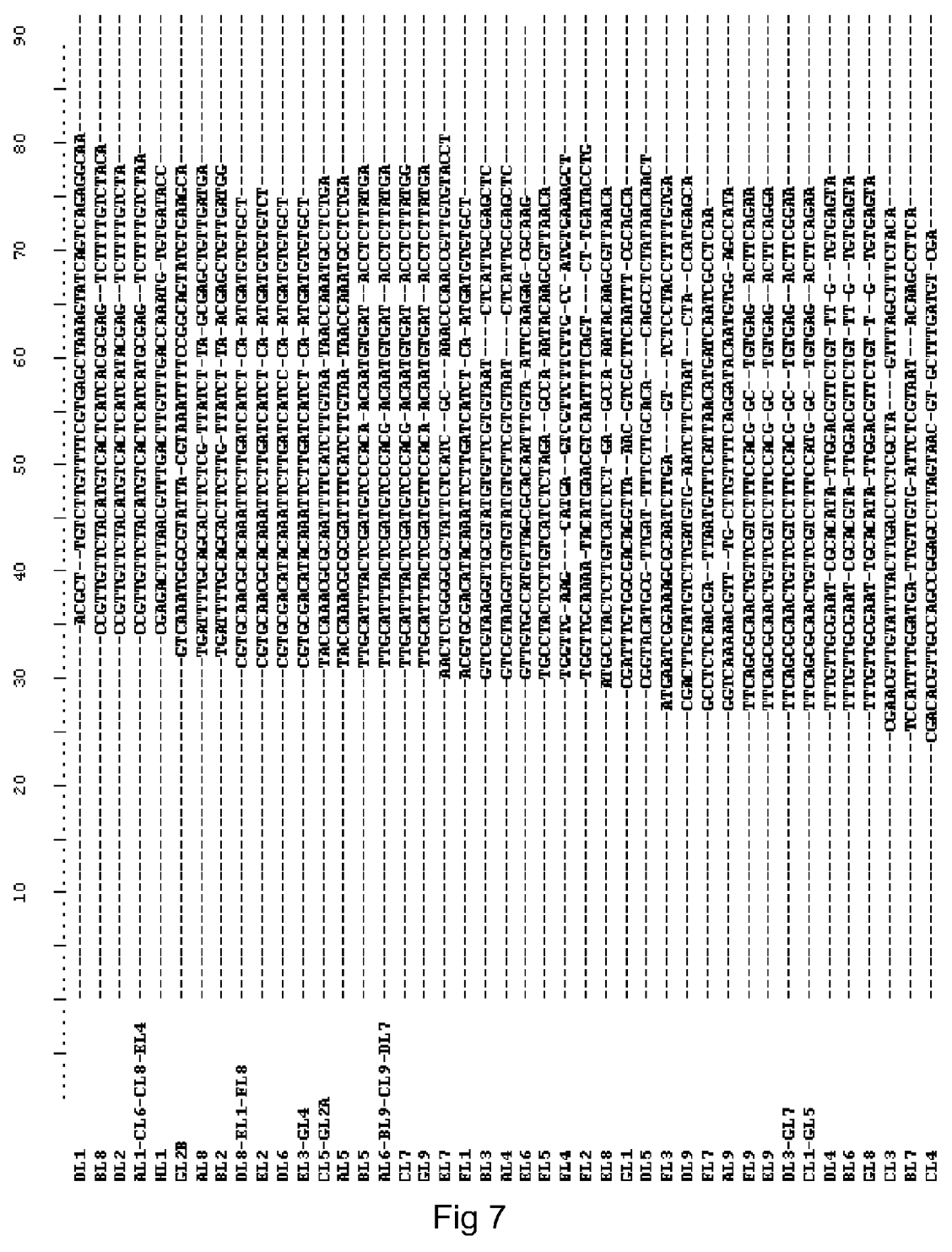

FIG. 7. Alignment of sequences obtained from Whole-cell SELEX on NSCLC. 55 sequences (codified as AL1, BL2, CL1 etc.) obtained from the selection were aligned and analyzed as described in the legend to FIG. 5. Out of 55 sequences, 43 are different. The sequences are reported as DNA and for simplicity, fixed-primer sequence at 5' and 3' extremities are removed.

| The sequence identifiers for sequences aligned in FIG. 7 are as follows, starting with DL1: | |
|---|---|
| | SEQ ID NO: |
| DL1 | 63 (codons 24-67) |
| BL8 | 64 (codons 24-67) |
| DL2 | 65 (codons 24-65) |
| AL1-CL6-CL8-EL4 | 66 (codons 24-66) |
| HL1 | 67 (codons 24-66) |
| GL2B | 68 (codons 24-68) |
| AL8 | 69 (codons 24-66) |
| BL2 | 70 (codons 24-66) |
| DL8-EL1-FL8 | 71 (codons 24-65) |
| EL2 | 72 (codons 24-66) |
| DL6 | 73 (codons 24-65) |
| EL3-GL4 | 74 (codons 24-65) |
| CL5-GL2A | 75 (codons 24-68) |
| AL5 | 76 (codons 24-68) |
| BL5 | 77 (codons 24-67) |
| AL6-BL9-CL9-DL7 | 78 (codons 24-67) |
| CL7 | 79 (codons 24-67) |
| GL9 | 80 (codons 24-67) |
| EL7 | 81 (codons 24-69) |
| FL1 | 82 (codons 24-66) |
| BL3 | 83 (codons 24-67) |
| AL4 | 84 (codons 24-67) |
| EL6 | 85 (codons 24-66) |
| FL5 | 86 (codons 24-66) |
| FL4 | 87 (codons 24-63) |
| FL2 | 88 (codons 24-67) |
| EL8 | 89 (codons 24-66) |
| GL1 | 90 (codons 24-66) |
| DL5 | 91 (codons 24-67) |
| FL3 | 92 (codons 24-66) |
| DL9 | 93 (codons 24-67) |
| FL7 | 94 (codons 24-68) |
| AL9 | 95 (codons 24-68) |
| FL9 | 96 (codons 24-67) |
| EL9 | 97 (codons 24-67) |
| DL3-GL7 | 98 (codons 24-67) |
| CL1-GL5 | 99 (codons 24-67) |
| DL4 | 100 (codons 24-67) |
| BL6 | 101 (codons 24-67) |
| GL8 | 102 (codons 24-66) |
| CL3 | 103 (codons 24-67) |
| BL7 | 104 (codons 24-67) |
| CL4 | 105 (codons 24-68) |

Figure 8:
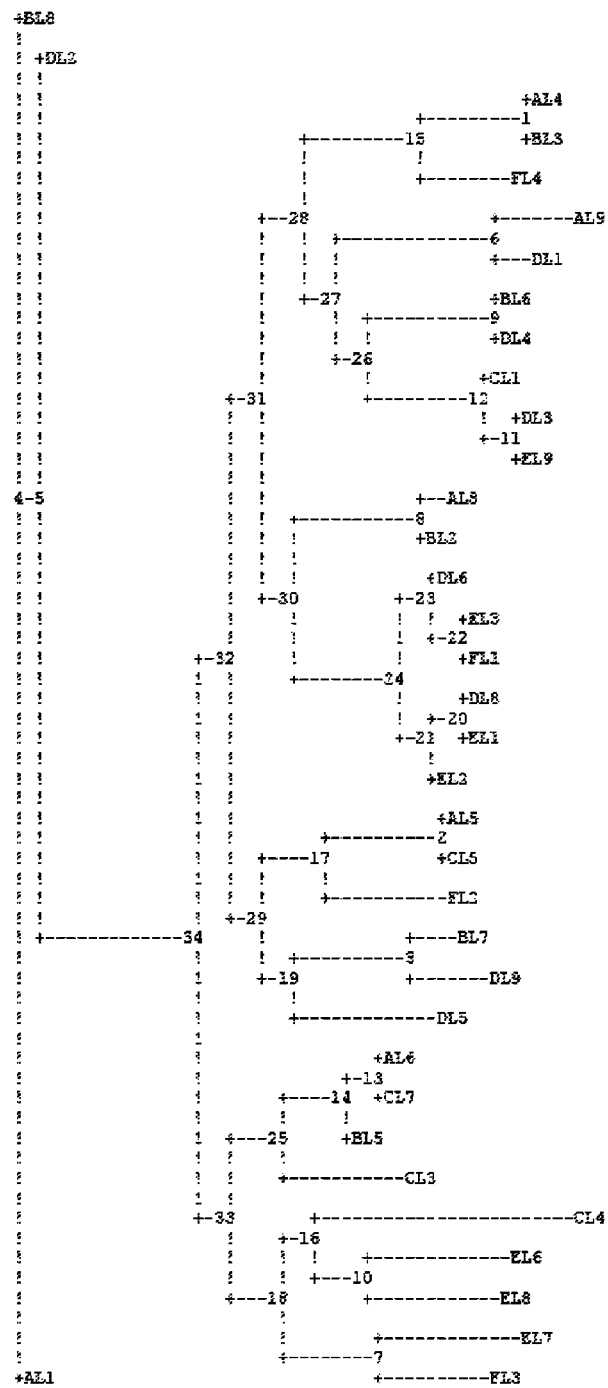

FIG. 8. Dendogram for visual classification of similarity among the 55 individual sequences cloned after the selection on NSCLC cells.

Figure 9:
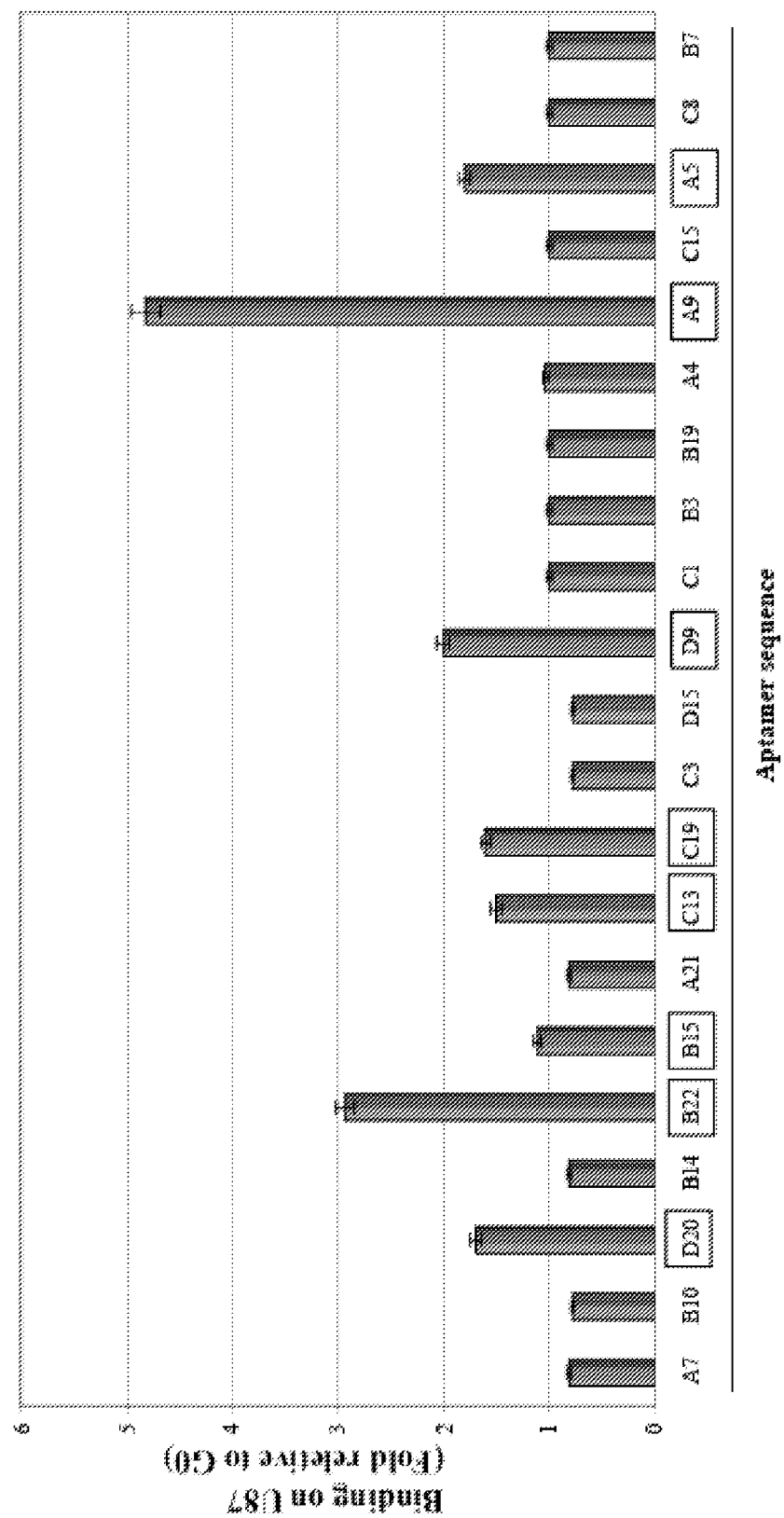

FIG. 9. First screening for binding properties of sequences obtained from Whole-cell SELEX on glioma cell lines. The indicated aptamers or the starting pool (G0) were 5'-[$^{32}$P]-labelled and incubated in the same condition at 500 nM on U87MG cells. The results are expressed relative to the background binding detected with the starting pool.

FIG. 10. Comparison of a secondary structure prediction for C13, A5, D9 and A9 aptamers. Predicted secondary structures for C13, A5, D9 and A9 aptamers (with fixed-primer sequence at extremities). Structures were predicted using MFOLD software version 3.1 (available at http://www.bioinfo.rpi.edu/applications/mfold/) (Zuker, 2003).

Figure 11:
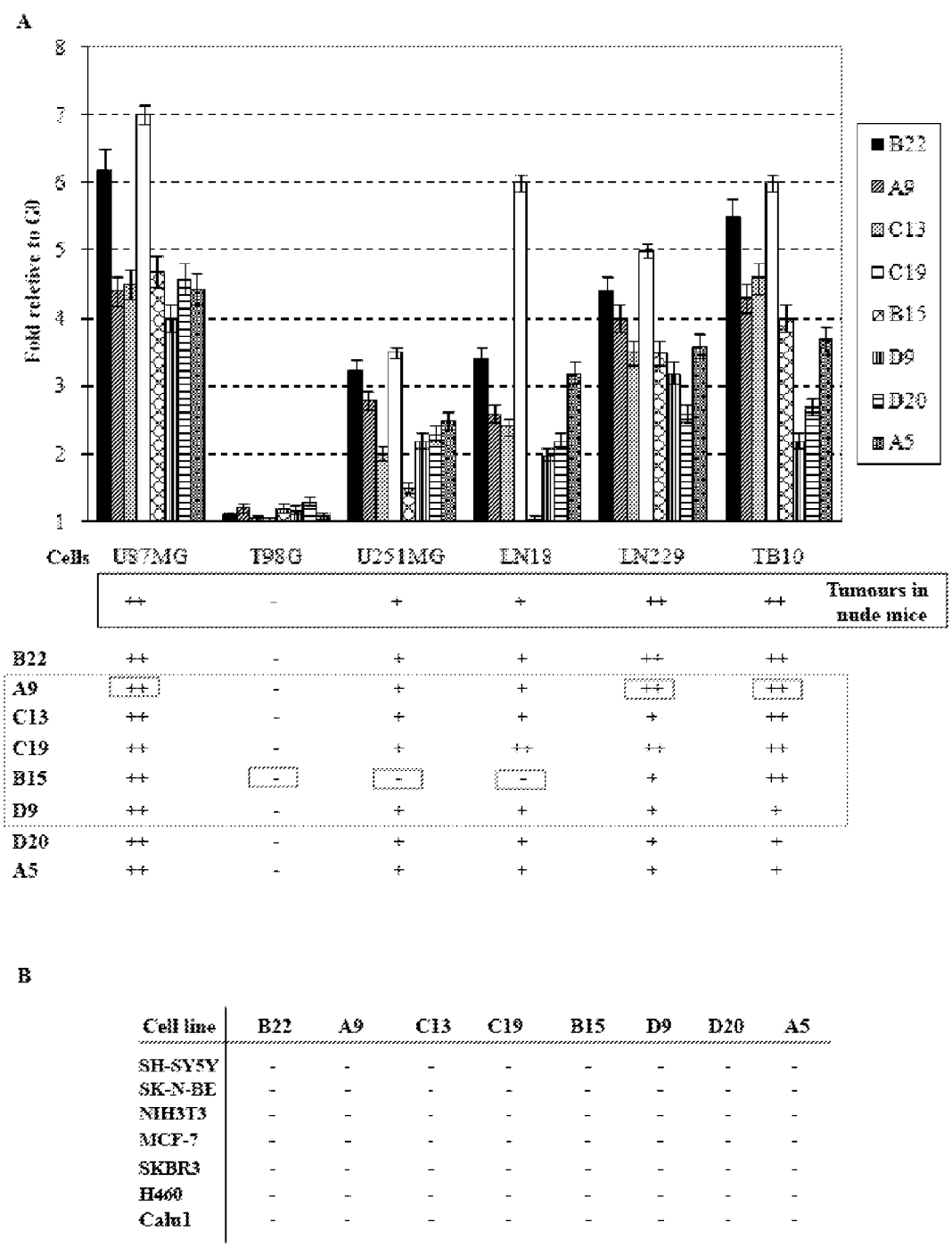

FIG. 11. Binding analyses of best sequences to glioma cell lines. The indicated aptamers or the starting pool (G0) were 5'-[$^{32}$P]-labeled and incubated in the same condition at 50 nM on the indicated glioma cell lines. The results are expressed relative to the background binding detected with the starting pool. The binding capacity of the aptamers to the cells is reported: high binding (more than four folds) is indicated as "++", middle binding (between two and four folds) is indicated as "+" and no binding (less than two folds) is indicated as "−". The tumorigenic potential in nude mice is indicated on the basis of the time of appearance of tumour and the tumour growth rate as previously reported (Ishii N et al (1999); Nishikawa R et at (1994); Pallini R et at (2006): high tumorigenicity is indicated as "++"; middle tumorigenicity is indicated as "+" and no tumorigenicity is indicated as "−").

FIG. 12. Biological activity of selected aptamers. U87MG cells were serum starved for 2 hs and either left untreated or treated for 1 h with 200 nM of the indicated RNA aptamer or the starting RNA pool (G0). (A) Cell lysates were immunoblotted with anti-pErk antibodies and then the filters were stripped and reprobed with anti-Erk antibodies to confirm equal loading. Quantitations are done on the sum of the two Erk-specific enhanced chemiluminescence bands of 44 and 42 kDa. (B) Cell lysates were immunoblotted with anti-pAkt, anti-Akt, anti-PDK1 and anti-pPDK1 antibodies. The filter were stripped and reprobed with anti-αtubulin antibodies to confirm equal loading. In A and B, intensity of bands have been calculated using the NIH Image Program on at least two different expositions to assure the linearity of each acquisition. Fold values are expressed relative to the reference points, arbitrarily set to 1 (labelled with asterisk). "C" indicates mock-treated cells.

FIG. 13. Time-course experiment of the best inhibitors. Serum starved U87MG cells were either left untreated or treated with 200 nM of the indicated RNA aptamers or G0 for the indicated incubation times. (A) Cell lysates were immunoblotted with anti-pcyclin D1 and cyclin D1 antibodies. To confirm equal loading the filters were stripped and reprobed with anti-αtubulin antibodies. (B) Cell lysates were immunoblotted with anti-pErk antibodies and the filters were stripped and reprobed with anti-Erk antibodies. In A and B, quantitation and relative abundances are expressed relative to controls, arbitrarily set to 1 (as reported in legend to FIG. 12); "C" indicates mock-treated cells. Plots of fold values corresponding to the cyclin D1 expression and to Erk activity are reported for each lane of immunoblotting shown in A and in B, respectively.

FIG. 14. CL4 aptamer from selection on NSCLC. (A) Predicted secondary structure for CL4 aptamer (with fixed-primer sequence at extremities). Structures were predicted using MFOLD software version 3.1. (B) To determine the binding affinity, the CL4 aptamer or the starting pool (G0) were 5'-[$^{32}$P]-labeled and incubated at different concentration on A459. The results are expressed relative to the background binding detected with the starting pool.

Figure 15:
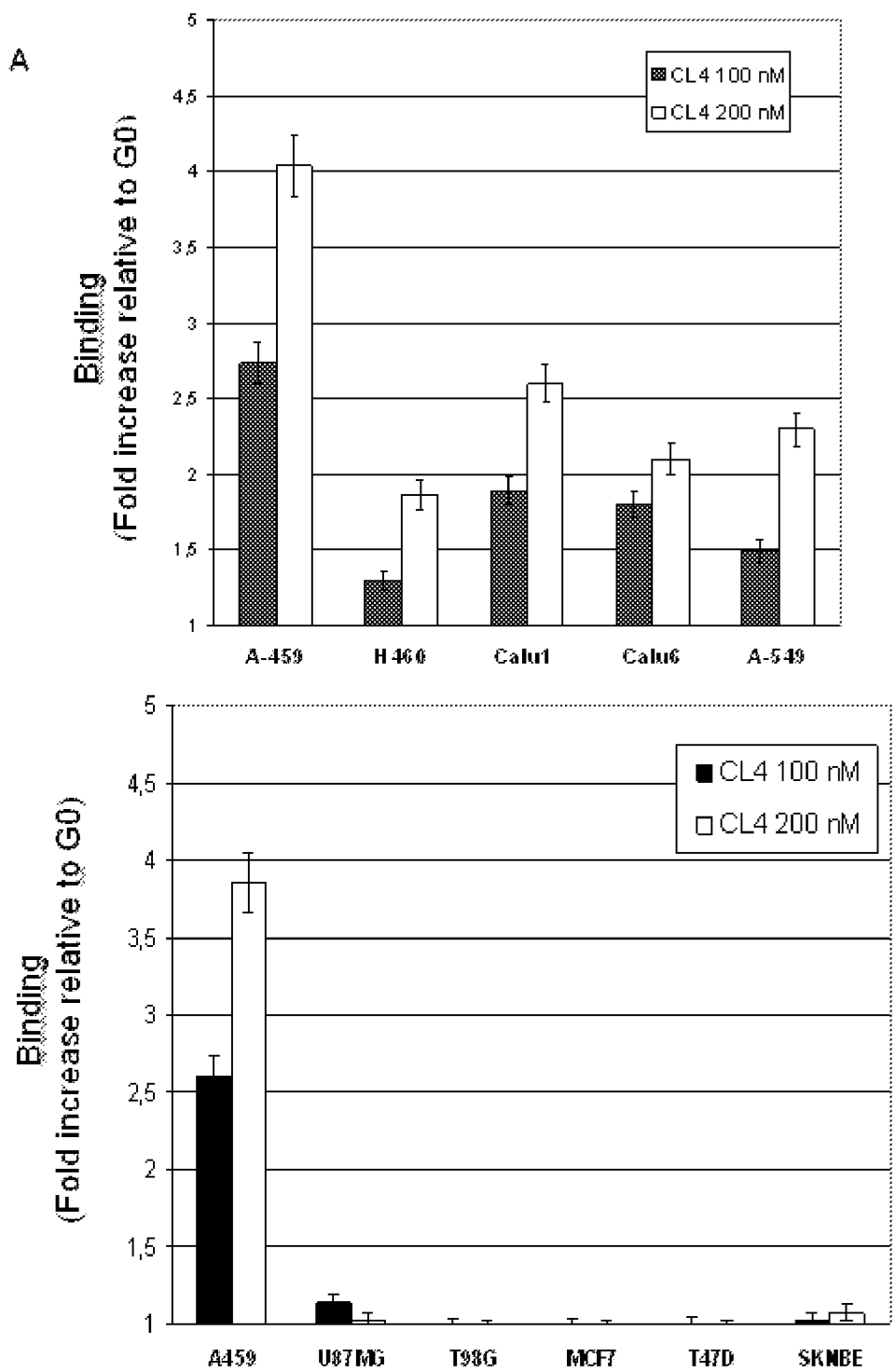
Figure 15:
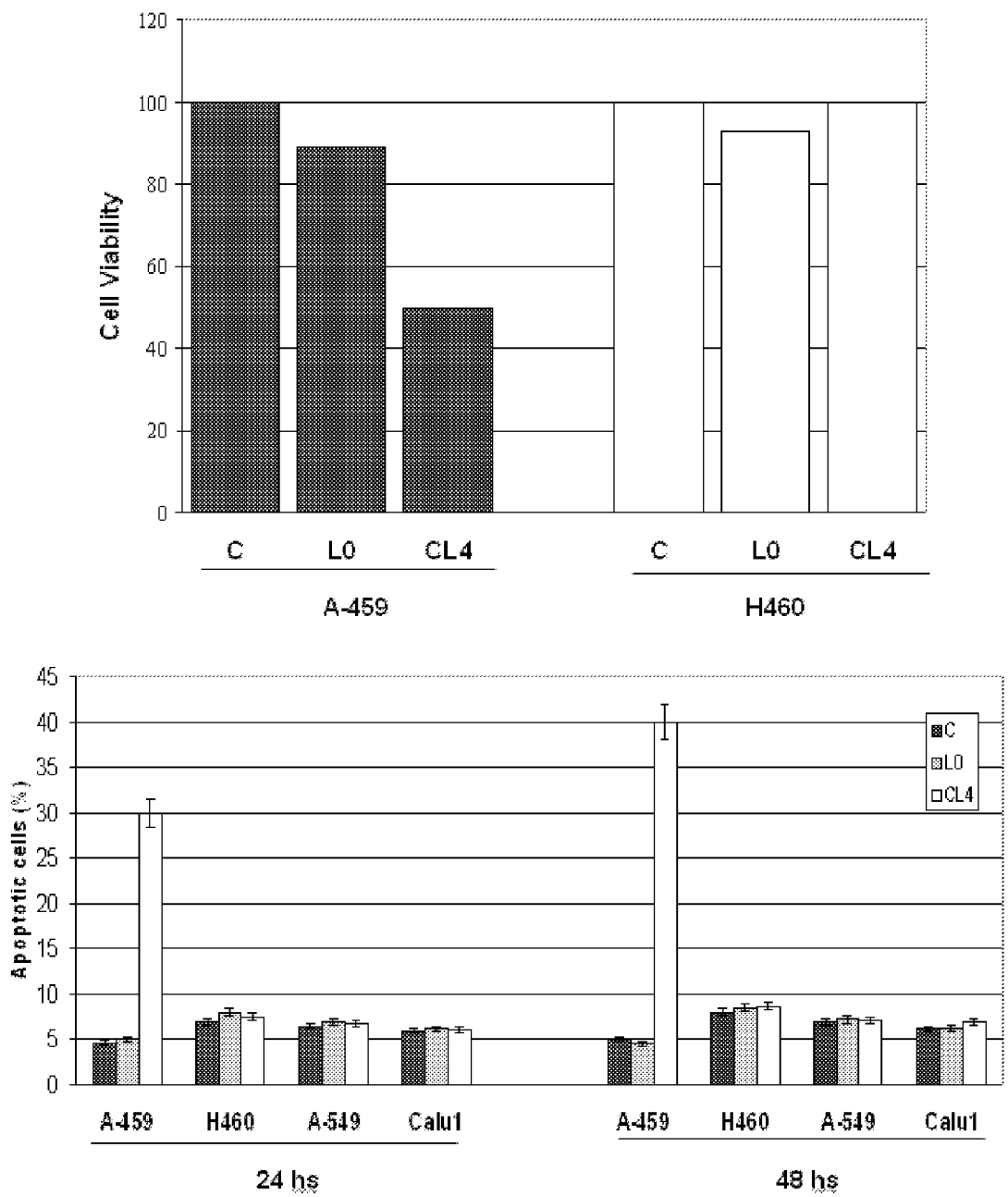

FIG. 15. Functional characterisation of CL4 pro-apoptotic aptamer. (A) CL4 aptamer or the starting pool (G0) were 5'-[$^{32}$P]-labeled and incubated in the same condition at 100 nM and 200 nM on the indicated human NSCLC cell lines (upper) or un-related cancer cell lines (lower). The results are expressed relative to the background binding detected with the starting pool. (B) CL4 has been incubated on the indicated NSCLC cells and cell viability has been assessed by MTT analyses following 24 hs (upper) or the percentage of apoptotic cells has been measured by FACS analyses following PI incorporation at 24 hs and 48 hs of treatment (lower).

FIG. 16. Design and characterisation of a shorten sequence. (A) Comparison of a secondary structure prediction for the A5, C13 aptamers and a shorten sequence consisting of residues 1-39 of these aptamers (short 1-39). (B) Binding affinity of the short (1-39) aptamer. To determine the binding affinity, the aptamer or the starting pool (G0) were 5'-[$^{32}$P]-labeled and incubated at different concentration on U87MG. The results are expressed relative to the background binding detected with the starting pool. (C) Biological activity of the short (1-39) aptamer. Serum starved U87MG cells were either left untreated or treated with 100 nM and 200 nM of the indicated RNA aptamers. Cell lysates were immunoblotted with Cyclin D1 antibodies. To confirm equal loading the filters were stripped and reprobed with anti-α-tubulin

METHODS

Cell Culture and Immunoblotting

Human glioma U87MG (American Type Culture Collection, ATCC no. HTB-14) and T98G (ATCC no. CRL-1690), U251MG and TB10 (kindly provided by A. Porcellini) cells were grown in Dulbecco's modified Eagle medium (DMEM) supplemented with 2 mM L-glutamine, 10% fetal bovine serum (Invitrogen, Carlsbad, Calif.). Human glioma, LN-18 (ATCC no. CRL-2610), LN-229 (ATCC no. CRL-2611) were grown in Advanced DMEM supplemented with 2 mM L-glutamine, 10% fetal bovine serum (Invitrogen, Carlsbad, Calif.). U87MG.ΔEGFR (Nishikawa R et al., 1994), a U87MG-derived cell line expressing a truncated mutant EGFR receptor due to an in-frame deletion of exons 2-7 from the extracellular domain (ΔEGFR or de 2-7 EGFR), were grown in DMEM supplemented with 2 mM L-glutamine, 10% fetal bovine serum, 500 µg/ml gentamycin (Invitrogen, Carlsbad, Calif.). Growth conditions for cell lines used were previously reported: human neuroblastoma SH-SY5Y and SK-N-BE cells (Esposito C L et al., 2008), human breast MCF7 and SKBR3 cells (Buckley M F et al., 1993), human NSCLC H460, Calu1, A459 and A549 cells (Zanca et al., 2008) and NIH3T3 cells (Cerchia et al., 2005)

To assess the functional effects of aptamers on U87MG cells, 300.000 cells per 3.5-cm plate were treated with the indicated amount of RNA aptamers or the starting RNA G0 pool after a short denaturation-renaturation step. Cell extracts and immunoblotting analysis were performed as described (Cerchia L et al., 2003). The primary antibodies used were: anti-ERK1 (C-16) (Santa Cruz Biotechnology, Santa Cruz, Calif., United States) and anti-phospho-44/42 MAP kinase (indicated as anti-pERK) monoclonal antibodies (E10), anti-Akt, anti-phospho-Akt (Ser473, indicated as anti-pAkt), anti-PDK1, anti-phospho-PDK1 (Ser241, indicated as anti-pPDK1), anti-phospho-cyclin D1 (Thr286, indicated as p-cyclin D1), anti-cyclin D1, all from Cell Signaling, Beverly, Mass., United States), anti-α-tubulin (DM 1A) (Sigma, St. Louis, Mo.). Four independent experiments were performed. Intensity of bands have been calculated using the NIH Image Program on at least two different expositions to assure the linearity of each acquisition. Fold values are expressed relative to the reference points, arbitrarily set to 1 (labelled with asterisk).

Cell Viability and Apoptosis Assays

NSCLC cell lines were plated in 96-well plates in triplicate and incubated at 37° C. in a 5% CO2 incubator. Cell were untreated or treated with CL4 or L0 starting poll as negative control at a final concentration of 200 nM.

Cell viability was evaluated following 24 hs of treatment with the CellTiter 96® AQueous One Solution Cell Proliferation Assay (Promega, Madison, Wis., USA), according to the manufacturer's protocol. Metabolically active cells were detected by adding 20 µl of MTS to each well. After 2 hrs of incubation, the plates were analysed in a Multilabel Counter (Bio-Rad).

Apoptosis was analyzed after 24 and 48 hs of CL4 treatment via propidium iodide incorporation in permeabilized cells by flow cytometry. The cells were washed in PBS and resuspended in 500 µl of a solution containing 0.1% sodium citrate, 0.1% Triton X-100 and 50 lg/ml propidium iodide (Sigma). Following incubation at 4° C. for 30 min in the dark, nuclei were analyzed with a Becton Dickinson FACScan flow cytometer. The percentage of elements in the hypodiploid region was calculated.

Whole-Cell SELEX

Transcription was performed in the presence of 1 mM 2'F-Py, 1 mM ATP, 1 mM GTP, 10 mM DTT, 0.5 u/µl RNAse inhibitors (Amersham Pharmacia), 10 µCi/µl $^{32}$P-αUTP (3000 Ci/mmol), 1 pmol/µl DNA and a mutant form of T7 RNA polymerase (2.5 u/µl T7 R&DNA polymerase, Epicentre) was used to improve yields. 2'F-Py RNAs were used because of their increased resistance to degradation by seric nucleases.

2'F-Py RNAs (800-300 pmol) were heated at 85° C. for 5 min in 1.5 ml of DMEM serum free, snap-cooled on ice for 2 min, and allowed to warm up to 37° C. Before incubation with the cells, 13.5 ml of medium were added to RNA to reach a final volume of 15 ml.

Glioma as Target

Counterselection Against T98G Cells

To avoid selecting for aptamers non-specifically recognizing the U87MG cell surface, the pool was first incubated for 30 min (up to round 9) or for 15 min (for the following rounds) at 37° C. with 10$^7$ T98G cells (150-mm cell plate), and unbound sequences were recovered for the selection phase. This step was meant to select sequences recognizing specifically the U87MG cells.

Selection Against U87MG Cells

The recovered sequences were incubated with 10$^7$ U87MG cells for 30 min at 37° C. and the U87MG-bound sequences were recovered after several washings with 5 ml of DMEM serum free by total RNA extraction (Ambion).

During the selection process, the authors progressively increased the selective pressure by increasing the number of washings (from one for the first cycle up to five for the last cycles) and by decreasing the incubation time (from 30 to 15 min from round 9). To follow the evolution of the pool the authors monitored the appearance of four-base restriction sites in the population by RFLP as previously described (Cerchia et al., 2005). After 14 rounds of selection, sequences were cloned with TOPO-TA cloning kit (Invitrogen, Carlsbad, Calif., United States) and analyzed.

NSCLC as Target

Counter-Selection on H460

To avoid selecting for aptamers non-specifically recognizing the A459 cell surface, the pool has been first incubated for 30 min (up to round 5) or for 15 min (for the following rounds) at 37° C. with 2×10$^6$ H460 cells (150-mm cell plate), and unbound sequences have been recovered for the selection phase.

Selection on A459

The sequences recovered from the counter-selection have been incubated with 2×10$^6$ A459 cells for 30 min (up to round 5) or for 15 min (for the following rounds) at 37° C. and the A459-bound sequences were recovered after several washings with DMEM serum free by total RNA extraction.

During the selection process, the authors progressively increased the selective pressure by: a) increasing the number of washings (from three for the first 9 cycles up to five for the last cycles); b) decreasing the incubation time (from 30 to 15 min starting from round 5); c) adding a second counter-selection step on H460 cells (from 1 to 2 counter-selections starting from round 4); d) adding polyI (polyinosinic acid) as a competitor for the last two selection cycles (round 13 and round 14).

Binding Analysis

Binding of individual aptamers (or of the starting pool as a control) to U87MG cells and T98G cells was performed in 24-well plates in triplicate with 5'-$^{32}$P-labeled RNA. 3.5×10$^4$ cells per well were incubated with various concentrations of individual aptamers in 200 µl of DMEM serum free for 20 min at RT in the presence of 100 µg/ml polyinosine as a nonspecific competitor (Sigma, St. Louis, Mo.). After five washings of 500 µl DMEM, bound sequences were recovered in 300 µl of SDS 1%, and the amount of radioactivity recovered was counted. The background values obtained with the starting pool were subtracted from the values obtained with the specific aptamers. Apparent Kd values for each aptamers were determined by Linewaver Burk analysis according to the equation:

$$1/[complex]=Kd/[Cmax]\times 1/[aptamer]+1/[Cmax].$$

Sequences (SEQ ID No. 1)
GGGAGACAAGAAUAAACGCUCAA fixed primer (SEQ ID No. 2)
UUCGACAGGAGGCUCACAACAGGC fixed primer Scheme 1 reports the aptamer's structure:
5' GGGAGACAAGAAUAAACGCUCAA (random sequence) UUC
GACAGGAGGCUCACAACAGGC 3'

Scheme 1
Glioma as target
B20
(SEQ ID No. 3)
GGGAGACAAGAAUAAACGCUCAAUCGUUUACAUUGUACUCUCCAUUAA

UGACCCUCGGAUUGCUUAGUUCGACAGGAGGCUCACAACAGGC

D7
(SEQ ID No. 4)
GGGAGACAAGAAUAAACGCUCAAACUAUCAAUGCCUGACGCACGAUAA

UCUUGCUGGUCUCACAGAAUUCGACAGGAGGCUCACAACAGGC

C4
(SEQ ID No. 5)
GGGAGACAAGAAUAAACGCUCAACCGCAAUGACUACCGUCUUGCAGUU

UUUAUAGCGUACUCUCAAUGUUCGACAGGAGGCUCACAACAGGC

C20
(SEQ ID No. 6)
GGGAGACAAGAAUAAACGCUCAACUGUCGAGCUUCAUUCAUGUGCUCA

CCGCUUACGCCUAAUGUCAUUUCGACAGGAGGCUCACAACAGGC

A2A21
(SEQ ID No. 7)
GGGAGACAAGAAUAAACGCUCAAUUGCAUUUACUCGAUGUCCCACGAC

AAUGUGAUACCUCUUAUGAUUCGACAGGAGGCUCACAACAGGC

C15
(SEQ ID No. 8)
GGGAGACAAGAAUAAACGCUCAAUUGCAUUUACUCGAUGUCCCACGAC

AAUGUGAUACCUCUUAUGAUUCGACAGGAGGCUCACAACAGGC

C24
(SEQ ID No. 9)
GGGAGACAAGAAUAAACGCUCAAUUGCAUUUACUCGAUGUCCCACGAC

AAUGUGAUACCUCUUAUAAUUCGACAGGAGGCUCACAACAGGC

C8
(SEQ ID No. 10)
GGGAGACAAGAAUAAACGCUCAAUUGCAUUUACUCGAUGUCCCACGAC

AAUGUGAUACCCCUCAAUUCGACAGGAGGCUCACAACAGGC

-continued

D14
(SEQ ID No. 11)
GGGAGACAAGAAUAAACGCUCAA**CGAACGUUGUAUUUACUUGACCUCG
CACUAGUUUAGCUUCCUACA**UUCGACAGGAGGCUCACAACAGGC

D6
(SEQ ID No. 12)
GGGAGACAAGAAUAAACGCUCAA**CGAACGUUGUAUUUACCUGACCUCU
CACUAGUUUAGCUUCCUACA**UUCGACAGGAGGCUCACAACAGGC

B10
(SEQ ID No. 13)
GGGAGACAAGAAUAAACGCUCAA**UGCACAUGAGUAUUUAUUCAUCUCA
AACGCUGACCUGCCAAUAA**UUCGACAGGAGGCUCACAACAGGC

A7
(SEQ ID No. 14)
GGGAGACAAGAAUAAACGCUCAACC**GUUGUUCUACAUGUCACUCAUCA
UGCGAGUCUUUUGUCUACA**UUCGACAGGAGGCUCACAACAGGC

B2
(SEQ ID No. 15)
GGGAGACAAGAAUAAACGCUCAA**CCGUUGUUCUACAUGUCAGUCAUCA
UGCGAGUCUUUUGUCUACAA**UUCGACAGGAGGCUCACAACAGGC

B19
(SEQ ID No. 16)
GGGAGACAAGAAUAAACGCUCAA**CCGUUGUUCUACAUGUCACUCAUCA
UGCGAGUCUUUUGUCUA**UUCGACAGGAGGCUCACAACAGGC

A6B15
(SEQ ID No. 17)
GGGAGACAAGAAUAAACGCUCAA**CCGUUGUUCUACAUGUCACUCAUCA
CGCGAGUCUUUUGUCUAA**UUCGACAGGAGGCUCACAACAGGC

C2
(SEQ ID No. 18)
GGGAGACAAGAAUAAACGCUCAA**UUGCCAAUACAGUUGAUCAUUGUCU
UACCAUUGACUAGUACC**UUCGACAGGAGGCUCACAACAGGC

C10
(SEQ ID No. 19)
GGGAGACAAGAAUAAACGCUCAA**CCCAAGUCAGUGAUUGGUAACUUUC
ACUUGACAAUAUCAAAUGCC**UUCGACAGGAGGCUCACAACAGGC

C1
(SEQ ID No. 20)
GGGAGACAAGAAUAAACGCUCAA**GCCUCUCAACGAUUAAUGUUUCAUU
AACAUGAUCAAUCGCCUCAA**UUCGACAGGAGGCUCACAACAGGC

B22
(SEQ ID No. 21)
GGGAGACAAGAAUAAACGCUCAA**GCCUCUCAACGAUUAAUGUUUCGUU
AACAUGAUCAAUCGCCUCAA**UUCGACAGGAGGCUCACAACAGGC

C5
(SEQ ID No. 22)
GGGAGACAAGAAUAAACGCUCAA**GGCAUUUGAUAUUGUCAAGUGAAAG
UUACCAAUCACUGAC**UUCGACAGGAGGCUCACAACAGGC

D23
(SEQ ID No. 23)
GGGAGACAAGAAUAAACGCUCAA**UUAUUAACGUUAUCAUUGUUCUUCA
CUACUUGUAGUACCUUCGA**UUCGACAGGAGGCUCACAACAGGC

C22
(SEQ ID No. 24)
GGGAGACAAGAAUAAACGCUCAA**CGUUAUUACUAUGUAUCACAACGUG
AACCCAUGUUGAAUCACAA**UUCGACAGGAGGCUCACAACAGGC

D2
(SEQ ID No. 25)
GGGAGACAAGAAUAAACGCUCAA**CCGUCUAUCGCGAAGCGUCUACUAU
CCUUGUUCAAUUGUGACUUC**UUCGACAGGAGGCUCACAACAGGC

B13
(SEQ ID No. 26)
GGGAGACAAGAAUAAACGCUCAA**CUGCACAGCGUCCACACAACUUGAU
CCACAAUUUUGAUGCCUUAU**UUCGACAGGAGGCUCACAACAGGC

B3
(SEQ ID No. 27)
GGGAGACAAGAAUAAACGCUCAA**CAACGAUGCUUGUUACGCGUAAUCU
UAGUCACAUUGCUUGCGU**UUCGACAGGAGGCUCACAACAGGC

C9
(SEQ ID No. 28)
GGGAGACAAGAAUAAACGCUCAA**CAACGAUGCUUGUUAUGCGUAAUCU
UAGUCACAUUGCUUGCGU**UUCGACAGGAGGCUCACAACAGGC

A20
(SEQ ID No. 29)
GGGAGACAAGAAUAAACGCUCAA**CACACGAUUGUUAUAAGCGCAUUAC
UCUCUGUCCCACUGUACUUGA**UUCGACAGGAGGCUCACAACAGGC

A2
(SEQ ID No. 30)
GGGAGACAAGAAUAAACGCUCAA**UAACGUGCUAUUCAGAACUUUGUCU
GCCCACUUUUAGUGAACUCCA**UUCGACAGGAGGCUCACAACAGGC

D3
(SEQ ID No. 31)
GGGAGACAAGAAUAAACGCUCAA**UCCAUUUUGGAUGAUCGUUGUGAUU
CUCGUAAUACAAGCCUUCA**UUCGACAGGAGGCUCACAACAGGC

C16
(SEQ ID No. 32)
GGGAGACAAGAAUAAACGCUCAA**CUAUCAAUAGUUGACAUCGUUCGCU
GUCUAUCGCAAUACUAUCC**UUCGACAGGAGGCUCACAACAGGC

C7
(SEQ ID No. 33)
GGGAGACAAGAAUAAACGCUCAA**CUUCAUGUUGAUCGCUUAUAAACUC
ACAUAGUUAGUCUCAUAA**UUCGACAGGAGGCUCACAACAGGC

C12
(SEQ ID No. 34)
GGGAGACAAGAAUAAACGCUCAA**UGAGUGUUAUCGAGUUGAUCGACAA
UACAAUCUCACAAUACCUUC**UUCGACAGGAGGCUCACAACAGGC

D9
(SEQ ID No. 35)
GGGAGACAAGAAUAAACGCUCAA**UACCAAACGCGCGGUUUUCGUCUCG
UAAUAACCAAAUGCCUCUGA**UUCGACAGGAGGCUCACAACAGGC

A9
(SEQ ID No. 36)
GGGAGACAAGAAUAAACGCUCAA**UACCAAACGCGCAAUUUUCAUCUUG
UAAUAACCAAAUGCCUCUGA**UUCGACAGGAGGCUCACAACAGGC

D21
(SEQ ID No. 37)
GGGAGACAAGAAUAAACGCUCAACAGUCGCGAAUUUUUUAUUCUUUCU
UACAACAAAGCAUAGCCUCAUUCGACAGGAGGCUCACAACAGGC

C18
(SEQ ID No. 38)
GGGAGACAAGAAUAAACGCUCAAGAUUGCGGAUUCUCAUCUUUCCAAC
AACGAACUAGCCUCUACUAUUCGACAGGAGGCUCACAACAGGC

C23
(SEQ ID No. 39)
GGGAGACAAGAAUAAACGCUCAAUUGUCAACGAUCGAGCACGUUCUCA
CACAAAGCCUCUUACUAUAUUCGACAGGAGGCUCACAACAGGC

C6
(SEQ ID No. 40)
GGGAGACAAGAAUAAACGCUCAACAAUCGCGUACGUUCUUGCGUAACA
AACAGCCACUGUCAUAAACUUCGACAGGAGGCUCACAACAGGC

D13
(SEQ ID No. 41)
GGGAGACAAGAAUAAACGCUCAACGUUUACGCGUAAUCUUGUAAUUCA
CAUUCUCUCAACAAGCCUAUUCGACAGGAGGCUCACAACAGGC

A4
(SEQ ID No. 42)
GGGAGACAAGAAUAAACGCUCAAGACAUCAACAUCUCAACGAUCUUGU
UACUCUCAACUCAAAUAGCUUCGACAGGAGGCUCACAACAGGC

A5
(SEQ ID No. 43)
GGGAGACAAGAAUAAACGCUCAAACGUUACUCUUGCAACACAAACUUU
AAUAGCCUCUUAUAGUUCUUCGACAGGAGGCUCACAACAGGC

A10C13
(SEQ ID No. 44)
GGGAGACAAGAAUAAACGCUCAAACUUACUCUUGCAACACCCAAACUU
UAAUAGCCUCUUAUAGUUCUUCGACAGGAGGCUCACAACAGGC

D18
(SEQ ID No. 45)
GGGAGACAAGAAUAAACGCUCAAACGUUACUCUUGCAACACCCAAACU
UUAAUAGCCUCUUACAGAAUUCGACAGGAGGCUCACAACAGGC

D5
(SEQ ID No. 46)
GGGAGACAAGAAUAAACGCUCAAUACAGCGCUAUUCUUCCAACCAAUC
AUACCACCUUGUCAUGUUAAUUCGACAGGAGGCUCACAACAGGC

C14
(SEQ ID No. 47)
GGGAGACAAGAAUAAACGCUCAACGAAUCGAAGCGAUAUUCCUUACCA
AUUAAUUGUAUAGCCUUAUUCGACAGGAGGCUCACAACAGGC

D19
(SEQ ID No. 48)
GGGAGACAAGAAUAAACGCUCAAUGUUGCAACAUCGAGUCAGCGUGUU
CUUCCAAGCCUCUAUAGAACUUCGACAGGAGGCUCACAACAGGC

D4
(SEQ ID No. 49)
GGGAGACAAGAAUAAACGCUCAACAUCGAAUACAGCCUUUAAUCCAAC
CUCCAAUUUCAAUCGACUAAUUCGACAGGAGGCUCACAACAGGC

B7
(SEQ ID No. 50)
GGGAGACAAGAAUAAACGCUCAAUUCAGCGAUGUUCUAAUCACCACAU
AACAAACUAUAGCCAGACCUUUCGACAGGAGGCUCACAACAGGC

B8
(SEQ ID No. 51)
GGGAGACAAGAAUAAACGCUCAAUGAUCGUUGAAUUCAACUGUCCACU
UAACAAAUUUCAGCCACUAAUUCGACAGGAGGCUCACAACAGGC

D22
(SEQ ID No. 52)
GGGAGACAAGAAUAAACGCUCAAUUCGUGUCAACUCAACCAACCAAGC
CUUCUGACGUACACUAAGUUCGACAGGAGGCUCACAACAGGC

C3C11D10
(SEQ ID No. 53)
GGGAGACAAGAAUAAACGCUCAAAACAGCGAUUCGAUCUCUACCCACAA
CACAAAUGCCUUCACACAUAUUCGACAGGAGGCUCACAACAGGC

B17
(SEQ ID No. 54)
GGGAGACAAGAAUAAACGCUCAAUGCGCGAAUUCUAUCCGUAUGCAAU
UCAUGCAUACAUUCCAACUAUUCGACAGGAGGCUCACAACAGGC

B14
(SEQ ID No. 55)
GGGAGACAAGAAUAAACGCUCAAUUAGAAUUCUAAUUUGAUAAUAUUA
CUUGCCGCCUCCACGAACACUUCGACAGGAGGCUCACAACAGGC

A3A1B4B8C19D11
(SEQ ID No. 56)
GGGAGACAAGAAUAAACGCUCAAUGAUUUUGCAGCACUUCUUGUUAUC
UUAACGAACUGUUGAUGAUUCGACAGGAGGCUCACAACAGGC

B16
(SEQ ID No. 57)
GGGAGACAAGAAUAAACGCUCAACUAAGAGGUUGACGCUUAGCACUUC
CAGUAACCUAAGCCUUCUAUUCGACAGGAGGCUCACAACAGGC

B4
(SEQ ID No. 58)
GGGAGACAAGAAUAAACGCUCAAUGUUUGACUUGAUUCUCUAGCUUAC
AAAUGUUAACAUCUGCAAAUUCGACAGGAGGCUCACAACAGGC

D12
(SEQ ID No. 59)
GGGAGACAAGAAUAAACGCUCAAUGUCUUGUUUAUUCGAACUCACAUU
AACAACAAUGAUUAGACGGCUUCGACAGGAGGCUCACAACAGGC

C21
(SEQ ID No. 60)
GGGAGACAAGAAUAAACGCUCAACCGCAACAAGAUUGACGGCUUGCGU
AAAUUCACAAGAUUUCAUUUUCGACAGGAGGCUCACAACAGGC

D15
(SEQ ID No. 61)
GGGAGACAAGAAUAAACGCUCAACUGUGACGACAGUUAAGAUCGUAUU
CUGCCACCAUACCUGUUGUAUUCGACAGGAGGCUCACAACAGGC

D1D20
(SEQ ID No. 62)
GGGAGACAAGAAUAAACGCUCAAUUCACACACUCAAUUGAACGGUGAU
UCAAGUUAUUAGCAGCCUCAUUCGACAGGAGGCUCACAACAGGC

M1
(SEQ ID No. 106)
GGGAGACAAGAAUAAACGCUCAAUGAUUGCGGAUUCUCAUCUUUCCAA
CAGCGAACUAGCCUCUACAUUCGACAGGAGGCUCACAACAGGC

M10
(SEQ ID No. 107)
GGGAGACAAGAAUAAACGCUCAAGGAAUCGAUCCGAUAAUUCGAUUCU
UUACAACAGCCUCACAAUAAUUCGACAGGAGGCUCACAACAGGC

M14
(SEQ ID No. 108)
GGGAGACAAGAAUAAACGCUCAAUGAUUUUGCAGCACUUCUUGUUAUC
UUAAUGAACUGUUGAUGAUUCGACAGGAGGCUCACAACAGGC

M16
(SEQ ID No. 109)
GGGAGACAAGAAUAAACGCUCAAGUCCCAAAUGUGACAGUUUAUUUAU
UGUCCAUAUCAUAAGCCUUUCGACAGGAGGCUCACAACAGGC

M18
(SEQ ID No. 110)
GGGAGACAAGAAUAAACGCUCAACGACACGUUGCCAGCCGGAGCCUUA
GUAACGUGCUUUGACGUCGAUUCGACAGGAGGCUCACAACAGGC

M20
(SEQ ID No. 111)
GGGAGACAAGAAUAAACGCUCAAUAACGGUAGACAUACGUGAUAUCUU
CAUAACCGUACUGCACGAUUCGACAGGAGGCUCACAACAGGC

M21
(SEQ ID No. 112)
GGGAGACAAGAAUAAACGCUCAAUGCAUACGGUGCAUUGUGCUCCAGC
CUCACACGAACGAUAAGAUUUCGACAGGAGGCUCACAACAGGC

M23
(SEQ ID No. 113)
GGGAGACAAGAAUAAACGCUCAACCGUUGUUCUACAUGUCACUCAUCA
UGCGAGUCUUUUGUCUAAUUUCGACAGGAGGCUCACAACAGGC

M25
(SEQ ID No. 114)
GGGAGACAAGAAUAAACGCUCAACUCGUGUGACCAACAUACCGCAUGA
AUUGACCGUUCUCAUUAAUUCGACAGGAGGCUCACAACAGGC

M26
(SEQ ID No. 115)
GGGAGACAAGAAUAAACGCUCAAUGCCGUGCCAUUAACACGCAUUCGA
AAUUUGCUGUCGUUACACAUUCGACAGGAGGCUCACAACAGGC

M6
(SEQ ID No. 116)
GGGAGACAAGAAUAAACGCUCAAUACCAAACGCGCAAUUUUCGUCUUG
UAAUAACCAAAUGCCUCUGAUUCGACAGGAGGCUCACAACAGGC

M33
(SEQ ID No. 117)
GGGAGACAAGAAUAAACGCUCAAUGAUUUUGCAGCACUUCUUGUUAUC
UUAACGAACAGUUGAUGAUUCGACAGGAGGCUCACAACAGGC

M35
(SEQ ID No. 118)
GGGAGACAAGAAUAAACGCUCAACUACCAUGACCUUAGCGCUUAUUGU
CUCGACCAUCAUCACAAUAAUUCGACAGGAGGCUCACAACAGGC

M39
(SEQ ID No. 119)
GGGAGACAAGAAUAAACGCUCAAAUCAAACGCGUCUUGUAAUCAUUCU
CUCUACCUUCACAUCGUAAUUCGACAGGAGGCUCACAACAGGC

M45
(SEQ ID No. 120)
GGGAGACAAGAAUAAACGCUCAAUGCAUACGGUGCAUUGUGCUUCAGC
CUCACACGAACGAUAAGAUUUCGACAGGAGGCUCACAACAGGC

M47
(SEQ ID No. 121)
GGGAGACAAGAAUAAACGCUCAAACAGCGAUUCGAUCUCUACCCACAA
CACAAAUGCCUUCACACAUGUUCGACAGGAGGCUCACAACAGGC

M48
(SEQ ID No. 122)
GGGAGACAAGAAUAAACGCUCAACGUGAACGUCUCACCAAUCGGAUAG
AAAUUGAUCAAGCCUAGUAAUUCGACAGGAGGCUCACAACAGGC

M51
(SEQ ID No. 123)
GGGAGACAAGAAUAAACGCUCAACGACACGUUGCCAGCCGGAGCCUUA
GUAACGUACUUUGAUGUCGAUUCGACAGGAGGCUCACAACAGGC

M52
(SEQ ID No. 124)
GGGAGACAAGAAUAAACGCUCAAUCAUCGAUUUCACAAUUGAGCUUCG
UAUCAGCCUCAACAAUUAUUUUCGACAGGAGGCUCACAACAGGC

M57
(SEQ ID No. 125)
GGGAGACAAGAAUAAACGCUCAAUGUCCAUUCAACAGAUUCUUUGUCU
UACCAAUCAGCCUUUACUUCGACAGGAGGCUCACAACAGGC

M62
(SEQ ID No. 126)
GGGAGACAAGAAUAAACGCUCAAUGAUUGCGGAUUCUCAUCUUUCCAA
CAACGAACUAGCCUCUACUAUUCGACAGGAGGCUCACAACAGGC

M63
(SEQ ID No. 127)
GGGAGACAAGAAUAAACGCUCAAAGAUCGAGUGCUAAUCUCAACAACG
AAAUCUAUGCGCCUCAAUAUUCGACAGGAGGCUCACAACAGGC

M65
(SEQ ID No. 128)
GGGAGACAAGAAUAAACGCUCAACAACGAAGCUUCUAUGUCUUGUUCA
GCUUAGCCUGUUCAACAUAAUUCGACAGGAGGCUCACAACAGGC

M70
(SEQ ID No. 129)
GGGAGACAAGAAUAAACGCUCAAAUGCGUCACACAAAUUGCUCUUAAC
UUUUGAGCCACUGCAGUAACAUUCGACAGGAGGCUCACAACAGGC

NSCLC as target
DL1
(SEQ ID No. 63)
GGGAGACAAGAAUAAACGCUCAAACGCUUGCUCUUGUUUUCGUGAGCUA
AAGUAUCAGUCAGAGGCAAUUCGACAGGAGGCUCACAACAGGC BL8
(SEQ ID No. 64)
GGGAGACAAGAAUAAACGCUCAACCGUUGUUCUACAUGUCACUCAUCA
CGCGAGUCUUUUGUCUACAUUCGACAGGAGGCUCACAACAGGC DL2
(SEQ ID No. 65)
GGGAGACAAGAAUAAACGCUCAACCGUUGUUCUACAUGUCACUCAUCA
UACGAGUCUUUUGUCUAUUCGACAGGAGGCUCACAACAGGC AL1-CL6-CL8-EL4
(SEQ ID No. 66)
GGGAGACAAGAAUAAACGCUCAACCGUUGUUCUACAUGUCACUCAUCA
UGCGAGUCUUUUGUCUAAUUCGACAGGAGGCUCACAACAGGC HL1
(SEQ ID No. 67)
GGGAGACAAGAAUAAACGCUCAACGAGACUUUAACGUUUGACUUGUUU
GACCAAAUGUGUGAUACCUUCGACAGGAGGCUCACAACAGGC GL2B
(SEQ ID No. 68)
GGGAGACAAGAAUAAACGCUCAAGUCAAAUGGGCGUAUUACGUAAAUU
UUCCGGCAGUAUGUGAAGCAUUCGACAGGAGGCUCACAACAGGC AL8
(SEQ ID No. 69)
GGGAGACAAGAAUAAACGCUCAAUGAUUUUGCAGCACUUCUCGUUAUC
UUAGCGAGCUGUUGAUGAUUCGACAGGAGGCUCACAACAGGC BL2
(SEQ ID No. 70)
GGGAGACAAGAAUAAACGCUCAAUGAUUUUGCAGCACUUCUUGUUAUC
UUAACGAGCUGUUGAUGGUUCGACAGGAGGCUCACAACAGGC DL8-EL1-FL8
(SEQ ID No. 71)
GGGAGACAAGAAUAAACGCUCAACGUGCAACGCACAAAUUCUUGAUCA
UCUCAAUGAUGUGUGCUUUCGACAGGAGGCUCACAACAGGC EL2
(SEQ ID No. 72)
GGGAGACAAGAAUAAACGCUCAACGUGCAACGCACAAAUUCUUGAUCA
UCUCAAUGAUGUGUGUCUUUCGACAGGAGGCUCACAACAGGC DL6
(SEQ ID No. 73)
GGGAGACAAGAAUAAACGCUCAACGUGCGACAUACAAAUUCUUGAUCA
UCCCAAUGAUGUGUGCUUUCGACAGGAGGCUCACAACAGGC EL3-GL4
(SEQ ID No. 74)
GGGAGACAAGAAUAAACGCUCAACGUGCGACAUACAAAUUCUUGAUCA
UCUCAAUGAUGUGUGCUUUCGACAGGAGGCUCACAACAGGC CL5-GL2A
(SEQ ID No. 75)
GGGAGACAAGAAUAAACGCUCAAUACCAAACGCGCAAUUUUCAUCUUG
UAAUAACCAAAUGCCUCUGAUUCGACAGGAGGCUCACAACAGGC AL5
(SEQ ID No. 76)
GGGAGACAAGAAUAAACGCUCAAUACCAAACGCGCGAUUUUCAUCUUG
UAAUAACCAAAUGCCUCUGAUUCGACAGGAGGCUCACAACAGGC BL5
(SEQ ID No. 77)
GGGAGACAAGAAUAAACGCUCAAUUGCAUUUACUCGAUGUCCCACAAC
AAUGUGAUACCUCUUAUGAUUCGACAGGAGGCUCACAACAGGC AL6-BL9-CL9-DL7
(SEQ ID No. 78)
GGGAGACAAGAAUAAACGCUCAAUUGCAUUUACUCGAUGUCCCACGAC
AAUGUGAUACCUCUUAUGAUUCGACAGGAGGCUCACAACAGGC CL7
(SEQ ID No. 79)
GGGAGACAAGAAUAAACGCUCAAUUGCAUUUACUCGAUGUCCCACGAC
AAUGUGAUACCUCUUAUGGUUCGACAGGAGGCUCACAACAGGC GL9
(SEQ ID No. 80)
GGGAGACAAGAAUAAACGCUCAAUUGCAUUUACUCGAUGUUCCACAAC
AAUGUGAUACCUCUUAUGAUUCGACAGGAGGCUCACAACAGGC EL7
(SEQ ID No. 81)
GGGAGACAAGAAUAAACGCUCAAAACUCUGGGGCGCUAUUCUCAUCGC
AAACCCAACCGUUGUGUACCUUUCGACAGGAGGCUCACAACAGGC FL1
(SEQ ID No. 82)
GGGAGACAAGAAUAAACGCUCAAACGUGCGACAUACAAAUUCUUGAUC
AUCUCAAUGAUGUGUGCUUUCGACAGGAGGCUCACAACAGGC BL3
(SEQ ID No. 83)
GGGAGACAAGAAUAAACGCUCAAGUCGUAAGGUUGCGUAUGUGUUCGU
GUAAUCUCAUUGCGAGCUCUUCGACAGGAGGCUCACAACAGGC AL4
(SEQ ID No. 84)
GGGAGACAAGAAUAAACGCUCAAGUCGUAAGGUUGUGUAUGUGUUCGU
GUAAUCUCAUUGCGAGCUCUUCGACAGGAGGCUCACAACAGGC EL6
(SEQ ID No. 85)
GGGAGACAAGAAUAAACGCUCAAGUUGUGCCAUGUUAGCGCACAAUUU
GUAAUUCAAGAGCGCAAGUUCGACAGGAGGCUCACAACAGGC FL5
(SEQ ID No. 86)
GGGAGACAAGAAUAAACGCUCAAUGCCUACUCUUGUCAUCUCUAGAGC
CAAAUACAAGCGUUAACAUUCGACAGGAGGCUCACAACAGGC FL4
(SEQ ID No. 87)
GGGAGACAAGAAUAAACGCUCAAUGGUUGAAGCAUGAGUCGUUCUUCU
UGCCAUGUGAAAGCUUUCGACAGGAGGCUCACAACAGGC FL2
(SEQ ID No. 88)
GGGAGACAAGAAUAAACGCUCAAUGGUUGCAAAAUACAUGAACGUCAA
UUUUCAGUCUUGAUACCUGUUCGACAGGAGGCUCACAACAGGC EL8
(SEQ ID No. 89)
GGGAGACAAGAAUAAACGCUCAAAUGCCUACUCUUGUCAUCUCUGAGC
CAAAUACAAGCGUUAACAUUCGACAGGAGGCUCACAACAGGC GL1
(SEQ ID No. 90)
GGGAGACAAGAAUAAACGCUCAACGAUUUGUGGCGACAGGUUAAACGU
CGCUUCAAUUUCGCAGCAUUCGACAGGAGGCUCACAACAGGC

```
DL5
                              (SEQ ID No. 91)
GGGAGACAAGAAUAAACGCUCAACGGUACAUGCGUUGAUUUUCUUGCA
CACAGCCUCUAUAACAACUUUCGACAGGAGGCUCACAACAGGC

FL3
                              (SEQ ID No. 92)
GGGAGACAAGAAUAAACGCUCAAAUGAAUCGGAAAGCGCAAUCUUGAG
UUCUCCUACCUUUUGUGAUUCGACAGGAGGCUCACAACAGGC

DL9
                              (SEQ ID No. 93)
GGGAGACAAGAAUAAACGCUCAACGACUUGUAUGUCUUGAUGUGAAUC
UUCUAAUCUACCAUGAGCAUUCGACAGGAGGCUCACAACAGGC

FL7
                              (SEQ ID No. 94)
GGGAGACAAGAAUAAACGCUCAAGCCUCUCAACGAUUAAUGUUUCAUU
AACAUGAUCAAUCGCCUCAAUUCGACAGGAGGCUCACAACAGGC

AL9
                              (SEQ ID No. 95)
GGGAGACAAGAAUAAACGCUCAAGGUCAAAAACGUUUGCUUGUUUUCA
GGAUACAAUGUGGAGCCAUAUUCGACAGGAGGCUCACAACAGGC

FL9
                              (SEQ ID No. 96)
GGGAGACAAGAAUAAACGCUCAAUUCAGCGCAACUGUUCGUCUUUCCA
CGGCUGUGAGACUUCAGAAUUCGACAGGAGGCUCACAACAGGC

EL9
                              (SEQ ID No. 97)
GGGAGACAAGAAUAAACGCUCAAUUCAGCGCAACUGUUCGUCUUUCCA
CGGCUGUGAGACUUCAGGAUUCGACAGGAGGCUCACAACAGGC

DL3-GL7
                              (SEQ ID No. 98)
GGGAGACAAGAAUAAACGCUCAAUUCAGCGCAACUGUUCGUCUUUCCA
CGGCUGUGAGACUUCGGAAUUCGACAGGAGGCUCACAACAGGC

CL1-GL5
                              (SEQ ID No. 99)
GGGAGACAAGAAUAAACGCUCAAUUCAGCGCAACUGUUCGUCUUUCCA
UGGCUGUGAGACUUCAGAAUUCGACAGGAGGCUCACAACAGGC

DL4
                              (SEQ ID No. 100)
GGGAGACAAGAAUAAACGCUCAAUUUGUUGCGAAUCGCACAUAUUGGA
CGUUCUGUUUGUGUGAGUAUUCGACAGGAGGCUCACAACAGGC

BL6
                              (SEQ ID No. 101)
GGGAGACAAGAAUAAACGCUCAAUUUGUUGCGAAUCGCACGUAUUGGA
CGUUCUGUUUGUGUGAGUAUUCGACAGGAGGCUCACAACAGGC

GL5
                              (SEQ ID No. 102)
GGGAGACAAGAAUAAACGCUCAAUUUGUUGCGAAUUGCACAUAUUGGA
CGUUCUGUUGUGUGAGUAUUCGACAGGAGGCUCACAACAGGC

CL3
                              (SEQ ID No. 106)
GGGAGACAAGAAUAAACGCUCAAGAACGUUGUAUUUACUUGACCUCUC
GCUAGUUUAGCUUUCUACAUUCGACAGGAGGCUCACAACAGGC

BL7
                              (SEQ ID No. 104)
GGGAGACAAGAAUAAACGCUCAAUCCAUUUUGGAUGAUUGUUGUGAUU
CUCGUAAUACAAGCCUUCAUUCGACAGGAGGCUCACAACAGGC

CL4
                              (SEQ ID No. 105)
GGGAGACAAGAAUAAACGCUCAACGACACGUUGCCAGCCGGAGCCUUA
GUAACGUGCUUUGAUGUCGAUUCGACAGGAGGCUCACAACAGGC
```

EXAMPLES

Example 1

Whole Cell SELEX Using Glioma Cells: Differential Whole Cell SELEX

Enrichment of Selection for a Complex Target, RFLP, Enrichment of Recovery, Differential Binding on Different Cell Lines In order to isolate cell specific ligands for a given tumor cell phenotype, the authors used as a model system, stable human glioma cell lines. Stable cell lines have the advantage that they can be kept under well controlled growth conditions and that they remain stable all along the SELEX procedure. The authors used as target for the selection steps the human malignant glioma cell line, U87MG and for the counterselection steps the T98G. These two cell lines differ for the potential to form tumors in nude mice and for resistance to radiation-induced cell death. U87MG being highly tumorigenic and radio-resistant while the T98G are poorly tumorigenic and sensitive to radiations. On the other hand, these cell lines share the same altered cellular pathways as both harbor $p14^{arf}/p16$ deletion and PTEN mutation. The major difference found between the two cell lines is the levels of ErbB2 and pErk, that are higher in U87MG than in T98G, while pAkt and NCAM levels are similar (data not shown). The relative levels of these four molecules were monitored at each cycle of the SELEX procedure to verify and standardize the growth conditions of the cells.

A library of 2'Fluoro Pyrimidines (2'F-Py), nuclease-resistant RNAs was utilized for differential SELEX against intact cells (FIG. 1). Each selection step on U87MG cells, was preceded by one or two counterselection steps against the T98G cells.

The method of the present invention is particularly efficient in selecting highly selective aptamers since at each SELEX cycle, the pool of aptamers is deprived of aptamers that recognize common cellular antigens present at high levels on the surface of both control and target cell lines. As a consequence, in the pool is impoverished of unwanted sequences, thus the aptamer for the specific rare antigens will be able to bind its target even if embedded in a complex target. The protocol consists of applying at each round one or more counterselection steps before each positive selection step.

During the selection process, the authors progressively increased the selective pressure by changing both incubation and washing conditions (FIG. 2A). Following each round the authors monitored the evolution of the pool by Restriction Fragment Length Polymorphism analysis (RFLP). After 8 rounds of selection, some sequences were predominantly amplified and dominated in abundance the aptamer pool, resulting in discrete restriction bands. During rounds 13 and 14, RFLP profiles remain unchanged, indicating an evolution of the sequence distribution in the library (FIG. 2B).

Cloning and Distribution of Individual Sequences

After 14 rounds of selection, the pool, named G14, was enriched for aptamers that preferentially bind to U87MG cells when compared with the in vitro binding efficiency on T98G cells and compared to the binding of the naïve starting pool (FIG. 3).

A panel of 71 sequences were cloned from the pool G14 and aptamers were grouped in families based on their primary sequence similarity (FIG. 5 and FIG. 6). The authors identified The authors identified ten families of highly related aptamers that together cover more than 46% (34 aptamers) of the all individual sequences obtained from the selection; an individual sequence, C19 (also codified as, A3, A1, B4, B8, D11), dominated the selection and constituted 8% of all the clones; five other sequences, C3 (also codified as C11 and D10), A6 (also codified as B15), A10 (also codified as C13) D1 (also codified as D20), A2 (also codified as A21) represented together more than 15% of the clones. The remaining 37 sequences were poorly related each other.

Using the starting pool as a control, binding of individual aptamers to U87MG and T98G cells was then performed. In order to screen for individual ligand aptamers that efficiently target U87MG cells, at least one member for each family (a total of 21 aptamers were tested) was first analysed at 500 nM. At this concentrations, 8 aptamers display up to a five-fold increase of binding to U87MG cells with respect to the starting pool, the remaining 13 aptamers having no specific binding for U87MG. The results are shown in FIG. 9.

As shown in Table 1, these 8 sequences bind at high affinity (with Kd ranging between 38 nM and 710 nM) the U87MG cells and have no or low affinity for T98G (not shown).

TABLE 1

Kd (nM) and Cmax (pM) of the best sequences

| Aptamer | Kd (nM) | Cmax (pM) |
|---------|---------|-----------|
| B15 | 102 ± 12 | 3400 ± 408 |
| B22 | 221 ± 25 | 4310 ± 495 |
| D20 | 710 ± 40 | 20000 ± 3400 |
| A5 | 44 ± 4 | 290 ± 26 |
| D9 | 43.7 ± 7 | 2100 ± 330 |
| C13 | 38 ± 3 | 2900 ± 232 |
| C19 | 63 ± 9 | 290 ± 41 |
| A9 | 190 ± 20 | 3410 ± 340 |

Bioinformatic Analysis of Individual Sequences

Four of the eight aptamers considered (B22, B15, C19 and D20) have unrelated primary sequences and predicted 2D folded structures. Two of them (C13 and A5) differ for the presence of two cytosine residues [C42 C43] that are only present in C13 whose presence however doesn't alter the affinity for the target cells (see Table 1). Consistently, the predicted secondary structures are unaltered by the presence of C42, C43 (FIG. 10). The opposite situation was found in another couple of aptamers (A9 and D9) that poorly differ in their primary structure but display different predicted secondary structures (FIG. 10). Interestingly, such difference changes also the binding affinity by 4,5 times. In fact, binding affinities reported in Table 1 shows a Kd of 43.7 nM for D9 and a Kd of 190 nM for A9. In FIG. 11 were reported the relative binding values at the same concentration for all aptamers, i.e. 50 nM.

Binding on Unrelated and Glioma Cell Lines

The identification of a small set of aptamers that may distinguish the U87MG cells from the T98G cells raises the obvious question of whether these aptamers may also bind to other cell types. To this aim, the authors determined the relative binding potential of each aptamer to several cell lines. The authors first determined the cell type specificity by measuring the binding of each aptamer on a panel of unrelated cell lines. They found that the aptamers did not bind to fibroblast NIH3T3 and did not recognize other cancer types including human neuroblastoma (SKNBE and SHSY5Y), lung (H460 and A459) and breast (MCF7 and SKBR3) cells (FIG. 11B). Further, the aptamers bind to different extents to glioma cell lines (U87MG, T98G, U251MG, TB10, LN-18, LN-229 and U87MG.ΔEGFR) characterised by different malignant phenotypes (FIG. 11A). At that aptamers concentration each glioma cell line has a distinct pattern of binding (see Legend). At these experimental conditions, all aptamers have good binding with the highly tumorigenic cell lines (U87MG, LN-229, U87MG.ΔEGFR and TB10), the aptamers C19 binds to all cell lines except the non tumorigenic T98G, and B15 binds only the four highly tumorigenic cell lines. Thus the pattern of binding of five of these aptamers (for example, C13, B15, C19, A9 and D9) is sufficient to distinguish two cell lines (see FIG. 11A).

Biological Activities

Biological activities of each aptamer have been thus verified in U87MG cells. As previously demonstrated for the anti RET receptor tyrosine kinase D4 aptamer, high affinity aptamer binding to an extracellular receptor may inhibit activity of downstream transducing molecules, as ERK family members. Therefore, the authors first determined whether any of the U87MG specific aptamer may interfere with the presence of the phosphorylated active Akt and Erk 1/2. Surprisingly, five of the tested aptamers (A9, D9, C13, A5 and B22) inhibited ERK phosphorylation, compared to the control starting pool and to the other aptamers (B15, C19, D20) (FIG. 12A). On the other hand no aptamer had any relevant effect on the phosphorylation of Akt and PDK1, likely because the U87MG harbor a mutated inactive PTEN, a phosphatase that negatively regulates the levels of Akt phosphorylation (FIG. 11B).

To further confirm the biological activity of A9, D9, C13, A5 and B22, the authors determined the extent of inhibition of expression of the cell cycle-related protein, cyclin D1 and of phosphorylation of ERK 1/2 upon treatment of U87MG cells with aptamers for increasing time periods. As shown in FIG. 13A, treatment with cognate aptamers either A9 and D9, or C13 and A5, inhibits at similar extents basal cyclin D1 expression and phosphorylation in a time dependent manner. Further, treating cells with the aptamer B22 resulted as well in a stronger and more rapid inhibition of cyclin D1 reaching around 26% at 1 h.

As shown in FIG. 13B treatment with the same five aptamers caused a similar time dependent inhibition of Erk phosphorylation. Inhibition being more rapid with D9 than A9, thus according to their respective Kd values (see Table 1), and, as expected, at comparable extents treating with the highly related C13 and A5 aptamers.

Example 2

Whole-Cell SELEX to Isolate RNA-Aptamers Against Trail-Resistant NSCLC

To extend the validity of the whole-cell SELEX approach to a different cell system, the authors have also performed the selection on NSCLC cells.

In order to generate RNA-aptamers able to discriminate between TRAIL-resistant and TRAIL-sensitive cell phenotype, the authors have selected for the SELEX method, two different cell lines of human lung carcinoma among four different NSCLC: A459, Calu1, H460, and A549.

These NSCLC have been extensively characterized for their resistance to the cytotoxic effects of TRAIL and it has been established that the human lung A459 (epidermoid lung carcinoma) cells (p53 null) are resistant to TRAIL, while the H460 (lung epithelial cell carcinoma) cells (wild type p53) are highly sensitive to TRAIL (Zanca C. et al., 2008).

Furthermore, these four NSCLC have been characterized for their expression of molecules participating in the apoptotic process and for their different sensitivity to the chemotherapies that are currently in use for the treatment of lung cancer: paclitaxel, cisplatinum, carboplatin, navelbine and gemcitabine. The experiments revealed that the cell lines tested are all resistant to cisplatinum, cambomplatinum, navelbine and gemcitabine. By contrast, they are characterised by different sensitivity to paclitaxel: two cell lines are resistant (A459, Calu1) and two are sensitive (H460, and A549). As a further characterization, the authors have performed immunoblotting analyses on cell extracts from the four cell lines and among them, Calu1 and H460 cells showed the highest and the lowest, respectively, levels of the analyzed proteins, for examples EGFR, PED, c-FLIP (not shown).

The authors applied the same approach as for glioma cells by using a selection step on A459 cells preceded by counterselection on H460.

RFLP analysis performed on the pool from each round of selection (named L1 to L14) and on the starting pool (L0) revealed stabilized profiles following 14 rounds of selection.

Example 3

Whole Cell SELEX Using NSCLC Cells: Differential Whole Cell SELEX

Enrichment of Selection for a Complex Target, RFLP, Enrichment of Recovery, Differential Binding on Different Cell Lines In order to isolate cell specific ligands for a given tumor cell phenotype, the authors used as a model system, stable human NSCLC cell lines. Stable cell lines have the advantage that they can be kept under well controlled growth conditions and that they remain stable all along the SELEX procedure. The authors used as target for the selection steps the human malignant NSCLC cell line, A459 and for the counterselection steps the H460. These NSCLC have been extensively characterized for their resistance to the cytotoxic effects of TRAIL and it has been established that the human lung A459 (adenocarcinoma) cells (wild type p53) are resistant to TRAIL, while the H460 (lung epithelial cell carcinoma) cells (wild type p53) are highly sensitive to TRAIL (Zanca C. et al., 2008 and authors personal communication).

Furthermore, we have characterised these two NSCLC for their different sensitivity to the chemotherapies that are currently in use for the treatment of lung cancer: paclitaxel, cisplatinum. The experiments revealed A459 are resistant to both chemotherapeutics while the H460 are sensitive. As a further characterization, the authors have performed immunoblotting analyses on cell extracts from two cell lines and A459 and H460 cells showed the highest and the lowest, respectively, levels of the analyzed proteins, for examples EGFR, PED, c-FLIP (not shown).

A library of 2'Fluoro Pyrimidines (2'F-Py), nuclease-resistant RNAs was utilized for differential SELEX against intact cells (FIG. 1). Each selection step on A459 cells was preceded by one or two counterselection steps against the H460 cells.

The method of the present invention is particularly efficient in selecting highly selective aptamers since at each SELEX cycle, the pool of aptamers is deprived of aptamers that recognize common cellular antigens present at high levels on the surface of both control and target cell lines. As a consequence, in the pool is impoverished of unwanted sequences, thus the aptamer for the specific rare antigens will be able to bind its target even if embedded in a complex target. The protocol consists of applying at each round one or more counterselection steps before each positive selection step.

During the selection process, the authors progressively increased the selective pressure by changing both incubation and washing conditions (FIG. 2A). Following each round the authors monitored the evolution of the pool by Restriction Fragment Length Polymorphism analysis (RFLP). After 5 rounds of selection, some sequences were predominantly amplified and dominated in abundance the aptamer pool, resulting in discrete restriction bands. During rounds 12, 13 and 14, RFLP profiles remain unchanged, indicating an evolution of the sequence distribution in the library (FIG. 2B).

Cloning and Distribution of Individual Sequences

After 14 rounds of selection, the pool, named L14, was enriched for aptamers that preferentially bind to A459 cells when compared with the in vitro binding efficiency on H460 cells and compared to the binding of the naïve starting pool (FIG. 4).

A panel of 42 sequences were cloned from the pool L14 and aptamers were grouped in families based on their primary sequence similarity (FIGS. 7 and 8). The authors identified 18 families of aptamers: 5 families cover more than 60% of all the individual sequences obtained from the selection; an individual sequence, C19 (also codified as, A3, A1, B4, B8, D11) dominated the selection and constituted 9% of all the clones; five sequences C19 (also codified as, A3, A1, B4, B8, D11), C3 (also codified as C11 and D10), A6 (also codified as B15), A10 (also codified as C13) D1 (also codified as D20) represented together more than 20% of the clones.

Example 4

Properties of NSCLC-Derived Aptamers

The selective induction of cell death by drugs or cytokines in cancer treatment is the goal of new therapeutic strategies. Apoptosis is believed to be the major mechanism of chemotherapy-induced cell death in cancer. However, tumour cells often retain the ability to evade drug-induced death signals but the mechanisms that determine resistance are largely unknown and it is therefore urgent to identify the molecules involved as potential therapeutic targets.

Biochemical Properties

The whole-cell SELEX procedure developed against non small cell lung carcinoma (NSCLC) let the authors to obtain a pool of aptamers that specifically bind to chemo-resistant A459 cells. The secondary structure prediction of one of these aptamers (named CL4) (including the fixed-primer sequences at extremities) was predicted by using MFOLD software (FIG. 14A). The authors have further characterized the binding activity and biological properties of the CL4 aptamer. As assessed by binding experiments, the CL4 aptamer displays a Kd of 46 nM on A459 cells (FIG. 14B) and has no or low affinity for H460 cells.

Binding on NSCLC and Unrelated Cell Lines

The identification of a small set of aptamers that may distinguish the A459 cells from the H460 cells raises the obvious question of whether these aptamers may also bind to other cell types. To this aim, using the starting pool as a control, the authors determined the relative binding potential of one of these aptamers, the CL4 aptamer to several cell lines. The aptamer binds to different extents to human NSCLC cell lines (A459, H460, Calu1, A549). As expected, the best binding was found with cells used for the selection, the A459, and the worst binding with cells used for counterselection, the H460. Further, the authors show that the CL4 aptamer binds at a very low extent to the human neuroblastoma, SKNBE and glioma, U87MG and T98G cell lines, and does not bind to the human breast MCF7 and T47D (FIG. 15A).

Biological Activity of CL4

Biological activities of the CL4 aptamer has been thus verified in A459 and H460 cells. By using a MTT assay, the authors first determined whether the CL4 may interfere with the cell viability. Interestingly, treating the A459 for 24 hrs, but not the cells used for counterselection, H460, inhibited the cell viability of around 60%. Inhibition was likely the consequence of increased apoptosis as shown by the induction of the percent of apoptotic cells as assessed by propidium iodine incorporation assay (FIG. 15B).

Example 5

Properties of Aptamer Derivatives

As mentioned above, four out of the eight aptamers from the Glioma selection (B22, B15, C19 and D20) have unrelated primary sequences and predicted 2D folded structures. Two (C13 and A5) differ for the presence of two cytosine residues (cyt42 and cyt43) that are only present in C13 whose presence however doesn't alter the affinity for the target cells (see Table 1). Comparing the predicted secondary structures defines a conserved stem-loop (residues 1-39) that is unaltered by the presence of cyt42 and cyt43. Consistently the shortened sequence, constituted of the first 39 residues, is sufficient to bind the U87MG cells (FIGS. 16A and B). In agreement with its Kd value, the shortened aptamer spanning the first 39 nucleotides of C13 or A5 aptamers, inhibited cyclin D1 expression and ERK phosphorylation at a similar extent as the C13 aptamer (FIG. 16C). This demonstrates that coupling bioinformatic information to the analysis of biochemical properties allows to reduce the size of aptamer molecules to make them suitable for in vivo use and to identify the target binding sites for each of them.

REFERENCES

Tuerk C. Gold L. Science 1990, 249, 505-510
Ellington and Szostak Nature 1990, 346: 818-22
Green L S et al., Chem Biol. 1995, 2 (10): 683-95
Tasset D M, Kubik M F, Steiner J., Mol. Biol. 1997, 272 (5): 688-98
Ruckman J, et al., J. Biol. Chem. 1998, 273 (32):20556-67
Cerchia et al., PLoS Biol. 2005, 3 (4):e123
Zuker, M. Nucleic Acids Res. 2003, 31, 3406-3415
Zanca C. et al., J Cell Mol. Med. 2008, February 15
Esposito C L, et al., PLoS ONE 2008, 3 (2):e1643
Buckley M F et al., Oncogene 1993, 8 (8):2127-33
Cerchia L, et al., Biochem J. 2003, 372: 897-903
Ishii N et al., Brain Pathol. 1999, 9: 469-79
Nishikawa R et al., Proc Nati Acad Sci. 1994, 91: 7727-31
Pallini R et al (2006) Int. J. Cancer 118: 2158-67

The invention claimed is:

1. A method for selecting a nucleic acid aptamer specific for a protein selectively expressed on the cell surface of target cells comprising the steps of:
   a) incubating a collection of synthetic nucleic acid oligoribonucleotide oligomers with human tumor derived counterselection control cells, allowing oligomers to bind to them
   b) recovering a first set of unbound nucleic acid oligomers;
   c) incubating the first set of unbound nucleic acid oligomers with human tumor derived target cells, allowing the first set of unbound nucleic acid oligomers to bind to them;
   d) recovering nucleic acid oligomers bound to the cell surface of target cells; and
   e) amplifying and sequencing the nucleic acid oligomers bound to the cell surface of target cells;
wherein the human tumor derived counterselection control cells of step a) are of the same cell type as the human tumor derived target cells of step c) but wherein the step a) cells exhibit a different phenotype with respect to the step c) cells.

2. The method of claim 1 wherein the first set of unbound nucleic acid oligomers recovered in step b) is incubated with the human tumor derived counterselection control cells and a second set of unbound nucleic acid oligomers recovered in step b) is further processed as indicated in steps c), d) and e).

3. The method according to claim 1 wherein the collection of synthetic nucleic acid oligoribonucleotide oligomers is a synthetic library.

4. The method according to claim 1 wherein the synthetic nucleic acid oligoribonucleotide oligomers are labeled.

5. The method according to claim 1 wherein the nucleic acid oligoribonucleotide oligomers are modified RNA-se resistant oligoribonucleotides.

6. The method according to claim 1 wherein the human tumor derived cells of step a) and step c) are glioma cells or NSCLC cells.

7. The method according to claim 1, wherein the difference in phenotype between the cells of step a) and the cells of step c) is selected from the group consisting of: resistance to a given physical or chemical therapeutic drug, tumor mass growth properties, apoptosis, and the ability to metastasize or degree of malignancy and therapeutic response.

8. The method according to claim 1 wherein the human tumor derived counterselection control cells of step a) are T98 cells or H460 cells.

9. The method according to claim 1 wherein the human tumor derived target cells of step c) are U87MG cells or A459 cells.

10. The method according to claim 1 wherein the human tumor derived counterselection control cells of step a) are poorly tumorigenic and the human tumor derived target cells of step c) are tumorigenic.

11. The method according to claim 1 wherein the human tumor derived counterselection control cells of step a) are radiation sensitive and the human tumor derived target cells of step c) are radiation resistant.

12. The method according to claim 1 wherein the human tumor derived counterselection control cells of step a) are sensitive to an chemotherapeutic anticancer agent and the human tumor derived target cells of step c) are insensitive to a chemotherapeutic anticancer agent.

13. The method according to claim 1 wherein the method consists of only a single counterselection step, according to step a).

* * * * *

SEQUENCE LISTING

<160> NUMBER OF SEQ ID NOS: 129

<210> SEQ ID NO 1
<211> LENGTH: 23
<212> TYPE: RNA
<213> ORGANISM: Artificial Sequence
<220> FEATURE:
<223> OTHER INFORMATION: synthetic primer/aptamer

<400> SEQUENCE: 1
gggagacaag aauaaacgcu caa                                              23

<210> SEQ ID NO 2
<211> LENGTH: 24
<212> TYPE: RNA
<213> ORGANISM: Artificial Sequence
<220> FEATURE:
<223> OTHER INFORMATION: synthetic primer/aptamer

<400> SEQUENCE: 2
uucgacagga ggcucacaac aggc                                             24

<210> SEQ ID NO 3
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 3
gggagacaag aauaaacgcu caaucguuua cauuguacuc uccauuaaug acccucggau       60
ugcuuaguuc gacaggaggc ucacaacagg c         91

<210> SEQ ID NO 4
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 4
gggagacaag aauaaacgcu caaacuauca augccugacg cacgauaauc uugcuggucu     60
cacagaauuc gacaggaggc ucacaacagg c         91

<210> SEQ ID NO 5
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 5
gggagacaag aauaaacgcu caaccgcaau gacuaccguc uugcaguuuu uauagcguac     60
ucucaauguu cgacaggagg cucacaacag gc         92

<210> SEQ ID NO 6
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 6
gggagacaag aauaaacgcu caacugucga gcuucauuca ugugcucacc gcuuacgccu     60
aaugucauuu cgacaggagg cucacaacag gc         92

<210> SEQ ID NO 7
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 7
gggagacaag aauaaacgcu caauugcauu uacucgaugu cccacgacaa ugugauaccu     60
cuuaugauuc gacaggaggc ucacaacagg c         91

<210> SEQ ID NO 8
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 8
gggagacaag aauaaacgcu caauugcauu uacucgaugu cccacgacaa ugugauaccu     60
cuuaugauuc gacaggaggc ucacaacagg c         91

<210> SEQ ID NO 9
<211> LENGTH: 91
<212> TYPE: RNA
<213> ORGANISM: Artificial Sequence
<220> FEATURE:
<223> OTHER INFORMATION: synthetic primer/aptamer

```
<400> SEQUENCE: 9
gggagacaag aauaaacgcu caauugcauu uacucgaugu cccacgacaa ugugauaccu    60
cuuauaauuc gacaggaggc ucacaacagg c                                   91

<210> SEQ ID NO 10
<211> LENGTH: 90
<212> TYPE: RNA
<213> ORGANISM: Artificial Sequence
<220> FEATURE:
<223> OTHER INFORMATION: synthetic primer/aptamer

<400> SEQUENCE: 10
gggagacaag aauaaacgcu caauugcauu uacucgaugu cccacgacaa ugugauaccc    60
ccucaauucg acaggaggcu cacaacaggc                                     90

<210> SEQ ID NO 11
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 11
gggagacaag aauaaacgcu caacgaacgu uguauuuacu ugaccucgca cuaguuuagc    60
uuccuacauu cgacaggagg cucacaacag gc                                  92

<210> SEQ ID NO 12
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 12
gggagacaag aauaaacgcu caacgaacgu uguauuuacc ugaccucuca cuaguuuagc    60
uuccuacauu cgacaggagg cucacaacag gc                                  92

<210> SEQ ID NO 13
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 13
gggagacaag aauaaacgcu caaugcacau gaguauuuau ucaucucaaa cgcugaccug    60
ccaauaauuc gacaggaggc ucacaacagg c                                   91

<210> SEQ ID NO 14
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 14
gggagacaag aauaaacgcu caaccguugu ucuacauguc acucaucaug cgagucuuuu    60
gucuacauuc gacaggaggc ucacaacagg c                                   91

<210> SEQ ID NO 15
<211> LENGTH: 92
<212> TYPE: RNA
```

```
<213> ORGANISM: Artificial Sequence
<220> FEATURE:
<223> OTHER INFORMATION: synthetic primer/aptamer

<400> SEQUENCE: 15
gggagacaag aauaaacgcu caaccguugu ucuacauguc agucaucaug cgagucuuuu    60
gucuacaauu cgacaggagg cucacaacag gc                                  92

<210> SEQ ID NO 16
<211> LENGTH: 90
<212> TYPE: RNA
<213> ORGANISM: Artificial Sequence
<220> FEATURE:
<223> OTHER INFORMATION: synthetic primer/aptamer

<400> SEQUENCE: 16
gggagacaag aauaaacgcu caaccguugu ucuacauguc acucaucaug cgagucuuuu    60
ugucuauucg acaggaggcu cacaacaggc                                     90

<210> SEQ ID NO 17
<211> LENGTH: 90
<212> TYPE: RNA
<213> ORGANISM: Artificial Sequence
<220> FEATURE:
<223> OTHER INFORMATION: synthetic primer/aptamer

<400> SEQUENCE: 17
gggagacaag aauaaacgcu caaccguugu ucuacauguc acucaucacg cgagucuuuu    60
gucuaauucg acaggaggcu cacaacaggc                                     90

<210> SEQ ID NO 18
<211> LENGTH: 89
<212> TYPE: RNA
<213> ORGANISM: Artificial Sequence
<220> FEATURE:
<223> OTHER INFORMATION: synthetic primer/aptamer

<400> SEQUENCE: 18
gggagacaag aauaaacgcu caauugccaa uacaguugau cauugcuuua ccauugacua    60
guaccuucga caggaggcuc acaacaggc                                      89

<210> SEQ ID NO 19
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 19
gggagacaag aauaaacgcu caacccaagu cagugauugg uaacuuucac uugacaauau    60
caaaugccuu cgacaggagg cucacaacag gc                                  92

<210> SEQ ID NO 20
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 20
gggagacaag aauaaacgcu caagccucuc aacgauuaau guucauuaa caugaucaau    60 cgccucaauu cgacaggagg cucacaacag gc                                  92
```

```
<210> SEQ ID NO 21
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 21
gggagacaag aauaaacgcu caagccucuc aacgauuaau guuucguuaa caugaucaau    60
cgccucaauu cgacaggagg cucacaacag gc                                 92

<210> SEQ ID NO 22
<211> LENGTH: 87
<212> TYPE: RNA
<213> ORGANISM: Artificial Sequence
<220> FEATURE:
<223> OTHER INFORMATION: synthetic primer/aptamer

<400> SEQUENCE: 22
gggagacaag aauaaacgcu caaggcauuu gauauuguca agugaaaguu accaaucacu    60
gacuucgaca ggaggcucac aacaggc                                       87

<210> SEQ ID NO 23
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 23
gggagacaag aauaaacgcu caauuauuaa cguuaucauu guucuucacu acuguagua    60 ccuucgauuc gacaggaggc ucacaacagg c                                  91

<210> SEQ ID NO 24
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 24
gggagacaag aauaaacgcu caacguuauu acuauguauc acaacgugaa cccauguuga    60
aucacaauuc gacaggaggc ucacaacagg c                                  91

<210> SEQ ID NO 25
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 25
gggagacaag aauaaacgcu caaccgucua ucgcgaagcg cuacuauccc uuguucaauu    60
gugacuucuu cgacaggagg cucacaacag gc                                 92

<210> SEQ ID NO 26
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 26
```

```
gggagacaag aauaaacgcu caacugcaca gcguccacac aacuugaucc acaauuuuga    60
ugccuuauuu cgacaggagg cucacaacag gc                                 92

<210> SEQ ID NO 27
<211> LENGTH: 90
<212> TYPE: RNA
<213> ORGANISM: Artificial Sequence
<220> FEATURE:
<223> OTHER INFORMATION: synthetic primer/aptamer

<400> SEQUENCE: 27
gggagacaag aauaaacgcu caacaacgau gcuuguuacg cguaaucuua gucacauugc    60
uugcguuucg acaggaggcu cacaacaggc                                    90

<210> SEQ ID NO 28
<211> LENGTH: 90
<212> TYPE: RNA
<213> ORGANISM: Artificial Sequence
<220> FEATURE:
<223> OTHER INFORMATION: synthetic primer/aptamer

<400> SEQUENCE: 28
gggagacaag aauaaacgcu caacaacgau gcuuguuaug cguaaucuua gucacauugc    60
uugcguuucg acaggaggcu cacaacaggc                                    90

<210> SEQ ID NO 29
<211> LENGTH: 93
<212> TYPE: RNA
<213> ORGANISM: Artificial Sequence
<220> FEATURE:
<223> OTHER INFORMATION: synthetic primer/aptamer

<400> SEQUENCE: 29
gggagacaag aauaaacgcu caacacacga uuguuauaag cgcauuacuc ucgucccac    60 uguacuugau ucgacaggag gcucacaaca ggc                                93

<210> SEQ ID NO 30
<211> LENGTH: 93
<212> TYPE: RNA
<213> ORGANISM: Artificial Sequence
<220> FEATURE:
<223> OTHER INFORMATION: synthetic primer/aptamer

<400> SEQUENCE: 30
gggagacaag aauaaacgcu caauaacgug cuauucagaa cuuugucugc ccacuuuuag    60
ugaacuccau ucgacaggag gcucacaaca ggc                                93

<210> SEQ ID NO 31
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 31
gggagacaag aauaaacgcu caauccauuu uggaugaucg uugugauucu cguaauacaa    60
gccuucauuc gacaggaggc ucacaacagg c                                  91

<210> SEQ ID NO 32
<211> LENGTH: 91
<212> TYPE: RNA
<213> ORGANISM: Artificial Sequence
<220> FEATURE:
```

<223> OTHER INFORMATION: synthetic primer/aptamer

<400> SEQUENCE: 32
gggagacaag aauaaacgcu caacuaucaa uaguugacau cguucgcugu cuaucgcaau    60
acuauccuuc gacaggaggc ucacaacagg c    91

<210> SEQ ID NO 33
<211> LENGTH: 90
<212> TYPE: RNA
<213> ORGANISM: Artificial Sequence
<220> FEATURE:
<223> OTHER INFORMATION: synthetic primer/aptamer

<400> SEQUENCE: 33
gggagacaag aauaaacgcu caacuucaug uugaucgcuu auaaacucac auaguuaguc    60
ucauaauucg acaggaggcu cacaacaggc    90

<210> SEQ ID NO 34
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 34
gggagacaag aauaaacgcu caaugagugu uaucgaguug aucgacaaua caaucucaca    60
auaccuucuu cgacaggagg cucacaacag gc    92

<210> SEQ ID NO 35
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 35
gggagacaag aauaaacgcu caauaccaaa cgcgcgguuu ucgucucgua auaaccaaau    60
gccucugauu cgacaggagg cucacaacag gc    92

<210> SEQ ID NO 36
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 36
gggagacaag aauaaacgcu caauaccaaa cgcgcaauuu ucaucuugua auaaccaaau    60
gccucugauu cgacaggagg cucacaacag gc    92

<210> SEQ ID NO 37
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 37
gggagacaag aauaaacgcu caacagucgc gaauuuuuua uucuuucuua caacaaagca    60
uagccucauu cgacaggagg cucacaacag gc    92

<210> SEQ ID NO 38

```
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 38
gggagacaag aauaaacgcu caagauugcg gauucucauc uuuccaacaa cgaacuagcc    60
ucuacuauuc gacaggaggc ucacaacagg c                                  91

<210> SEQ ID NO 39
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 39
gggagacaag aauaaacgcu caauugucaa cgaucgagca cguucucaca caaagccucu    60
uacuauauuu cgacaggagg cucacaacag gc                                 92

<210> SEQ ID NO 40
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 40
gggagacaag aauaaacgcu caacaaucgc guacguucuu gcguaacaaa cagccacugu    60
cauaaacuuc gacaggaggc ucacaacagg c                                  91

<210> SEQ ID NO 41
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 41
gggagacaag aauaaacgcu caacguuuac gcguaaucuu guaauucaca uucucucaac    60
aagccuauuc gacaggaggc ucacaacagg c                                  91

<210> SEQ ID NO 42
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 42
gggagacaag aauaaacgcu caagacauca acaucucaac gaucuuguua cucucaacuc    60
aaauagcuuc gacaggaggc ucacaacagg c                                  91

<210> SEQ ID NO 43
<211> LENGTH: 90
<212> TYPE: RNA
<213> ORGANISM: Artificial Sequence
<220> FEATURE:
<223> OTHER INFORMATION: synthetic primer/aptamer

<400> SEQUENCE: 43
gggagacaag aauaaacgcu caaacguuac ucuugcaaca caaacuuuaa uagccucuua    60
```

-continued uaguucuucg acaggaggcu cacaacaggc                                              90

<210> SEQ ID NO 44
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 44
gggagacaag aauaaacgcu caaacguuac ucuugcaaca cccaaacuuu aauagccucu         60
uauaguucuu cgacaggagg cucacaacag gc                                           92

<210> SEQ ID NO 45
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 45
gggagacaag aauaaacgcu caaacguuac ucuugcaaca cccaaacuuu aauagccucu         60
uacagaauuc gacaggaggc ucacaacagg c                                            91

<210> SEQ ID NO 46
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 46
gggagacaag aauaaacgcu caauacagcg cuauucuucc aaccaaucau accaccuugu         60
cauguuaauu cgacaggagg cucacaacag gc                                           92

<210> SEQ ID NO 47
<211> LENGTH: 90
<212> TYPE: RNA
<213> ORGANISM: Artificial Sequence
<220> FEATURE:
<223> OTHER INFORMATION: synthetic primer/aptamer

<400> SEQUENCE: 47
gggagacaag aauaaacgcu caacgaaucg aagcgauauu ccuuaccaau uaauuguaua         60
gccuuauucg acaggaggcu cacaacaggc                                              90

<210> SEQ ID NO 48
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 48
gggagacaag aauaaacgcu caauguugca acaucgaguc agcguguucu uccaagccuc         60
uauagaacuu cgacaggagg cucacaacag gc                                           92

<210> SEQ ID NO 49
<211> LENGTH: 92
<212> TYPE: RNA
<213> ORGANISM: Artificial Sequence
<220> FEATURE:
<223> OTHER INFORMATION: synthetic primer/aptamer -continued

```
<400> SEQUENCE: 49
gggagacaag aauaaacgcu caacaucgaa uacagccuuu aauccaaccu ccaauuucaa    60
ucgacuaauu cgacaggagg cucacaacag gc                                 92

<210> SEQ ID NO 50
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 50
gggagacaag aauaaacgcu caauucagcg auguucuaau caccacauaa caaacuauag    60
ccagaccuuu cgacaggagg cucacaacag gc                                 92

<210> SEQ ID NO 51
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 51
gggagacaag aauaaacgcu caaugaucgu ugaauucaac uguccacuua acaaauuuca    60
gccacuaauu cgacaggagg cucacaacag gc                                 92

<210> SEQ ID NO 52
<211> LENGTH: 90
<212> TYPE: RNA
<213> ORGANISM: Artificial Sequence
<220> FEATURE:
<223> OTHER INFORMATION: synthetic primer/aptamer

<400> SEQUENCE: 52
gggagacaag aauaaacgcu caauucgugu caacucaacc aaccaagccu ucgacguac    60 acuaaguucg acaggaggcu cacaacaggc                                   90

<210> SEQ ID NO 53
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 53
gggagacaag aauaaacgcu caaacagcga uucgaucucu acccacaaca caaaugccuu    60
cacacauauu cgacaggagg cucacaacag gc                                 92

<210> SEQ ID NO 54
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 54
gggagacaag aauaaacgcu caaugcgcga auucuauccg uaugcaauuc augcauacau    60
uccaacuauu cgacaggagg cucacaacag gc                                 92

<210> SEQ ID NO 55
<211> LENGTH: 92
<212> TYPE: RNA
```

```
<213> ORGANISM: Artificial Sequence
<220> FEATURE:
<223> OTHER INFORMATION: synthetic primer/aptamer

<400> SEQUENCE: 55
gggagacaag aauaaacgcu caauuagaau ucuaauuuga uaauauuacu ugccgccucc     60
acgaacacuu cgacaggagg cucacaacag gc                                  92

<210> SEQ ID NO 56
<211> LENGTH: 90
<212> TYPE: RNA
<213> ORGANISM: Artificial Sequence
<220> FEATURE:
<223> OTHER INFORMATION: synthetic primer/aptamer

<400> SEQUENCE: 56
gggagacaag aauaaacgcu caaugauuuu gcagcacuuc uuguuaucuu aacgaacugu     60
ugaugauucg acaggaggcu cacaacaggc                                     90

<210> SEQ ID NO 57
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 57
gggagacaag aauaaacgcu caacuaagag guugacgcuu agcacuucca guaaccuaag     60
ccuucuauuc gacaggaggc ucacaacagg c                                   91

<210> SEQ ID NO 58
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 58
gggagacaag aauaaacgcu caauguuuga cuugauucuc uagcuuacaa auguuaacau     60
cugcaaauuc gacaggaggc ucacaacagg c                                   91

<210> SEQ ID NO 59
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 59
gggagacaag aauaaacgcu caaugucuug uuuauucgaa cucacauuaa caacaaugau     60
uagacggcuu cgacaggagg cucacaacag gc                                  92

<210> SEQ ID NO 60
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 60
gggagacaag aauaaacgcu caaccgcaac aagauugacg gcuugcguaa auucacaaga     60
uuucauuuuc gacaggaggc ucacaacagg c                                   91
```

```
<210> SEQ ID NO 61
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 61
gggagacaag aauaaacgcu caacugugac gacaguuaag aucguauucu gccaccauac     60
cuguuguauu cgacaggagg cucacaacag gc                                  92

<210> SEQ ID NO 62
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 62
gggagacaag aauaaacgcu caauucacac acucaauuga acggugauuc aaguuauuag     60
cagccucauu cgacaggagg cucacaacag gc                                  92

<210> SEQ ID NO 63
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 63
gggagacaag aauaaacgcu caaacgcuug ucuuguuuuc gugagcuaaa guaucaguca     60
gaggcaauuc gacaggaggc ucacaacagg c                                   91

<210> SEQ ID NO 64
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 64
gggagacaag aauaaacgcu caaccguugu ucuacauguc acucaucacg cgagcuuuu      60 gucuacauuc gacaggaggc ucacaacagg c                                   91

<210> SEQ ID NO 65
<211> LENGTH: 89
<212> TYPE: RNA
<213> ORGANISM: Artificial Sequence
<220> FEATURE:
<223> OTHER INFORMATION: synthetic primer/aptamer

<400> SEQUENCE: 65
gggagacaag aauaaacgcu caaccguugu ucuacauguc acucaucaua cgagucuuuu     60
gucuauucga caggaggcuc acaacaggc                                      89

<210> SEQ ID NO 66
<211> LENGTH: 90
<212> TYPE: RNA
<213> ORGANISM: Artificial Sequence
<220> FEATURE:
<223> OTHER INFORMATION: synthetic primer/aptamer

<400> SEQUENCE: 66
```

```
gggagacaag aauaaacgcu caaccguugu ucuacauguc acucaucaug cgagucuuuu    60
gucuaauucg acaggaggcu cacaacaggc                                     90
```

<210> SEQ ID NO 67
<211> LENGTH: 90
<212> TYPE: RNA
<213> ORGANISM: Artificial Sequence
<220> FEATURE:
<223> OTHER INFORMATION: synthetic primer/aptamer

<400> SEQUENCE: 67

```
gggagacaag aauaaacgcu caacgagacu uuaacguuug acuuguuuga ccaaaugugu    60
gauaccuucg acaggaggcu cacaacaggc                                     90
```

<210> SEQ ID NO 68
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 68

```
gggagacaag aauaaacgcu caagucaaau gggcguauua cguaaauuuu ccggcaguau    60
gugaagcauu cgacaggagg cucacaacag gc                                  92
```

<210> SEQ ID NO 69
<211> LENGTH: 90
<212> TYPE: RNA
<213> ORGANISM: Artificial Sequence
<220> FEATURE:
<223> OTHER INFORMATION: synthetic primer/aptamer

<400> SEQUENCE: 69

```
gggagacaag aauaaacgcu caaugauuuu gcagcacuuc ucguuaucuu agcgagcugu    60
ugaugauucg acaggaggcu cacaacaggc                                     90
```

<210> SEQ ID NO 70
<211> LENGTH: 90
<212> TYPE: RNA
<213> ORGANISM: Artificial Sequence
<220> FEATURE:
<223> OTHER INFORMATION: synthetic primer/aptamer

<400> SEQUENCE: 70

```
gggagacaag aauaaacgcu caaugauuuu gcagcacuuc uuguuaucuu aacgagcugu    60
ugaugguucg acaggaggcu cacaacaggc                                     90
```

<210> SEQ ID NO 71
<211> LENGTH: 89
<212> TYPE: RNA
<213> ORGANISM: Artificial Sequence
<220> FEATURE:
<223> OTHER INFORMATION: synthetic primer/aptamer

<400> SEQUENCE: 71

```
gggagacaag aauaaacgcu caacgugcaa cgcacaaauu cuugaucauc ucaaugaugu    60
gugcuuucga caggaggcuc acaacaggc                                      89
```

<210> SEQ ID NO 72
<211> LENGTH: 90
<212> TYPE: RNA
<213> ORGANISM: Artificial Sequence
<220> FEATURE:

<223> OTHER INFORMATION: synthetic primer/aptamer

<400> SEQUENCE: 72
gggagacaag aauaaacgcu caacgugcaa cgcacaaauu cuugaucauc ucaaugaugu    60
gugucuuucg acaggaggcu cacaacaggc    90

<210> SEQ ID NO 73
<211> LENGTH: 89
<212> TYPE: RNA
<213> ORGANISM: Artificial Sequence
<220> FEATURE:
<223> OTHER INFORMATION: synthetic primer/aptamer

<400> SEQUENCE: 73
gggagacaag aauaaacgcu caacgugcga cauacaaauu cuugaucauc ccaaugaugu    60
gugcuuucga caggaggcuc acaacaggc    89

<210> SEQ ID NO 74
<211> LENGTH: 89
<212> TYPE: RNA
<213> ORGANISM: Artificial Sequence
<220> FEATURE:
<223> OTHER INFORMATION: synthetic primer/aptamer

<400> SEQUENCE: 74
gggagacaag aauaaacgcu caacgugcga cauacaaauu cuugaucauc ucaaugaugu    60
gugcuuucga caggaggcuc acaacaggc    89

<210> SEQ ID NO 75
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 75
gggagacaag aauaaacgcu caauaccaaa cgcgcaauuu ucaucuugua auaaccaaau    60
gccucugauu cgacaggagg cucacaacag gc    92

<210> SEQ ID NO 76
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 76
gggagacaag aauaaacgcu caauaccaaa cgcgcgauuu ucaucuugua auaaccaaau    60
gccucugauu cgacaggagg cucacaacag gc    92

<210> SEQ ID NO 77
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 77
gggagacaag aauaaacgcu caauugcauu uacucgaugu cccacaacaa ugugauaccu    60
cuuaugauuc gacaggaggc ucacaacagg c    91

<210> SEQ ID NO 78

```
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 78
gggagacaag aauaaacgcu caauugcauu uacucgaugu cccacgacaa ugugauaccu    60
cuuaugauuc gacaggaggc ucacaacagg c                                  91

<210> SEQ ID NO 79
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 79
gggagacaag aauaaacgcu caauugcauu uacucgaugu cccacgacaa ugugauaccu    60
cuuaugguuc gacaggaggc ucacaacagg c                                  91

<210> SEQ ID NO 80
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 80
gggagacaag aauaaacgcu caauugcauu uacucgaugu uccacaacaa ugugauaccu    60
cuuaugauuc gacaggaggc ucacaacagg c                                  91

<210> SEQ ID NO 81
<211> LENGTH: 93
<212> TYPE: RNA
<213> ORGANISM: Artificial Sequence
<220> FEATURE:
<223> OTHER INFORMATION: synthetic primer/aptamer

<400> SEQUENCE: 81
gggagacaag aauaaacgcu caaaacucug gggcgcuauu cucaucgcaa acccaaccgu    60
uguguaccuu ucgacaggag gcucacaaca ggc                                93

<210> SEQ ID NO 82
<211> LENGTH: 90
<212> TYPE: RNA
<213> ORGANISM: Artificial Sequence
<220> FEATURE:
<223> OTHER INFORMATION: synthetic primer/aptamer

<400> SEQUENCE: 82
gggagacaag aauaaacgcu caaacgugcg acauacaaau ucuugaucau cucaaugaug    60
ugugcuuucg acaggaggcu cacaacaggc                                    90

<210> SEQ ID NO 83
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 83
gggagacaag aauaaacgcu caagucguaa gguugcguau guguucgugu aaucucauug    60
```

```
cgagcucuuc gacaggaggc ucacaacagg c                                   91

<210> SEQ ID NO 84
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 84
gggagacaag aauaaacgcu caagucguaa gguuguguau guguucgugu aaucucauug    60
cgagcucuuc gacaggaggc ucacaacagg c                                   91

<210> SEQ ID NO 85
<211> LENGTH: 90
<212> TYPE: RNA
<213> ORGANISM: Artificial Sequence
<220> FEATURE:
<223> OTHER INFORMATION: synthetic primer/aptamer

<400> SEQUENCE: 85
gggagacaag aauaaacgcu caaguugugc cauguuagcg cacaauuugu aauucaagag    60
cgcaaguucg acaggaggcu cacaacaggc                                     90

<210> SEQ ID NO 86
<211> LENGTH: 90
<212> TYPE: RNA
<213> ORGANISM: Artificial Sequence
<220> FEATURE:
<223> OTHER INFORMATION: synthetic primer/aptamer

<400> SEQUENCE: 86
gggagacaag aauaaacgcu caaugccuac ucuugucauc ucuagagcca aauacaagcg    60
uuaacauucg acaggaggcu cacaacaggc                                     90

<210> SEQ ID NO 87
<211> LENGTH: 87
<212> TYPE: RNA
<213> ORGANISM: Artificial Sequence
<220> FEATURE:
<223> OTHER INFORMATION: synthetic primer/aptamer

<400> SEQUENCE: 87
gggagacaag aauaaacgcu caaugguuga agcaugraguc guucuucuug ccaugugaaa   60
gcuuucgaca ggaggcucac aacaggc                                        87

<210> SEQ ID NO 88
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 88
gggagacaag aauaaacgcu caaugguugc aaaauacaug aacgucaauu uucagucuug    60
auaccuguuc gacaggaggc ucacaacagg c                                   91

<210> SEQ ID NO 89
<211> LENGTH: 90
<212> TYPE: RNA
<213> ORGANISM: Artificial Sequence
<220> FEATURE:
<223> OTHER INFORMATION: synthetic primer/aptamer
```

```
<400> SEQUENCE: 89
gggagacaag aauaaacgcu caaaugccua cucuugucau cucugagcca aauacaagcg    60
uuaacauucg acaggaggcu cacaacaggc                                    90

<210> SEQ ID NO 90
<211> LENGTH: 90
<212> TYPE: RNA
<213> ORGANISM: Artificial Sequence
<220> FEATURE:
<223> OTHER INFORMATION: synthetic primer/aptamer

<400> SEQUENCE: 90
gggagacaag aauaaacgcu caacgauuug uggcgacagg uuaaacgucg cuucaauuuc    60
gcagcauucg acaggaggcu cacaacaggc                                    90

<210> SEQ ID NO 91
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 91
gggagacaag aauaaacgcu caacgguaca ugcguugauu uucuugcaca cagccucuau    60
aacaacuuuc gacaggaggc ucacaacagg c                                  91

<210> SEQ ID NO 92
<211> LENGTH: 90
<212> TYPE: RNA
<213> ORGANISM: Artificial Sequence
<220> FEATURE:
<223> OTHER INFORMATION: synthetic primer/aptamer

<400> SEQUENCE: 92
gggagacaag aauaaacgcu caaaugaauc ggaaagcgca aucuugaguu cuccuaccuu    60
uugugauucg acaggaggcu cacaacaggc                                    90

<210> SEQ ID NO 93
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 93
gggagacaag aauaaacgcu caacgacuug uaugucuuga ugugaaucuu cuaaucuacc    60
augagcauuc gacaggaggc ucacaacagg c                                  91

<210> SEQ ID NO 94
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 94
gggagacaag aauaaacgcu caagccucuc aacgauuaau guucauuaa caugaucaau    60 cgccucaauu cgacaggagg cucacaacag gc                                 92

<210> SEQ ID NO 95
<211> LENGTH: 92
<212> TYPE: RNA
```

```
<213> ORGANISM: Artificial Sequence
<220> FEATURE:
<223> OTHER INFORMATION: synthetic primer/aptamer

<400> SEQUENCE: 95
gggagacaag aauaaacgcu caaggucaaa aacguuugcu uguuucagg auacaaugug    60 gagccauauu cgacaggagg cucacaacag gc                                 92

<210> SEQ ID NO 96
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 96
gggagacaag aauaaacgcu caauucagcg caacuguucg ucuuccacg gcugugagac    60 uucagaauuc gacaggaggc ucacaacagg c                                  91

<210> SEQ ID NO 97
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 97
gggagacaag aauaaacgcu caauucagcg caacuguucg ucuuccacg gcugugagac    60 uucaggauuc gacaggaggc ucacaacagg c                                  91

<210> SEQ ID NO 98
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 98
gggagacaag aauaaacgcu caauucagcg caacuguucg ucuuccacg gcugugagac    60 uucggaauuc gacaggaggc ucacaacagg c                                  91

<210> SEQ ID NO 99
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 99
gggagacaag aauaaacgcu caauucagcg caacuguucg ucuuccaug gcugugagac    60 uucagaauuc gacaggaggc ucacaacagg c                                  91

<210> SEQ ID NO 100
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 100
gggagacaag aauaaacgcu caauuuguug cgaaucgcac auauuggacg uucuguuugu    60
gugaguauuc gacaggaggc ucacaacagg c                                  91
```

<210> SEQ ID NO 101
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 101
gggagacaag aauaaacgcu caauuuguug cgaaucgcac guauuggacg uucuguuugu    60
gugaguauuc gacaggaggc ucacaacagg c                                   91

<210> SEQ ID NO 102
<211> LENGTH: 90
<212> TYPE: RNA
<213> ORGANISM: Artificial Sequence
<220> FEATURE:
<223> OTHER INFORMATION: synthetic primer/aptamer

<400> SEQUENCE: 102
gggagacaag aauaaacgcu caauuuguug cgaaugcac auauuggacg uucuguugug     60
ugaguauucg acaggaggcu cacaacaggc                                     90

<210> SEQ ID NO 103
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 103
gggagacaag aauaaacgcu caagaacguu guauuuacuu gaccucucgc uaguuuagcu    60
uucuacauuc gacaggaggc ucacaacagg c                                   91

<210> SEQ ID NO 104
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 104
gggagacaag aauaaacgcu caauccauuu uggaugauug uugugauucu cguaauacaa    60
gccuucauuc gacaggaggc ucacaacagg c                                   91

<210> SEQ ID NO 105
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 105
gggagacaag aauaaacgcu caacgacacg uugccagccg gagccuuagu aacgugcuuu    60
gaugucgauu cgacaggagg cucacaacag gc                                  92

<210> SEQ ID NO 106
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 106

```
gggagacaag aauaaacgcu caaugauugc ggauucucau cuuuccaaca gcgaacuagc    60
cucuacauuc gacaggaggc ucacaacagg c                                  91
```

<210> SEQ ID NO 107
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 107

```
gggagacaag aauaaacgcu caaggaaucg auccgauaau ucgauucuuu acaacagccu    60
cacaauaauu cgacaggagg cucacaacag gc                                 92
```

<210> SEQ ID NO 108
<211> LENGTH: 90
<212> TYPE: RNA
<213> ORGANISM: Artificial Sequence
<220> FEATURE:
<223> OTHER INFORMATION: synthetic primer/aptamer

<400> SEQUENCE: 108

```
gggagacaag aauaaacgcu caaugauuuu gcagcacuuc uuguuaucuu aaugaacugu    60
ugaugauucg acaggaggcu cacaacaggc                                    90
```

<210> SEQ ID NO 109
<211> LENGTH: 90
<212> TYPE: RNA
<213> ORGANISM: Artificial Sequence
<220> FEATURE:
<223> OTHER INFORMATION: synthetic primer/aptamer

<400> SEQUENCE: 109

```
gggagacaag aauaaacgcu caagucccaa augugacagu uuauuuauug uccauaucau    60
aagccuuucg acaggaggcu cacaacaggc                                    90
```

<210> SEQ ID NO 110
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 110

```
gggagacaag aauaaacgcu caacgacacg uugccagccg gagccuuagu aacgugcuuu    60
gacgucgauu cgacaggagg cucacaacag gc                                 92
```

<210> SEQ ID NO 111
<211> LENGTH: 90
<212> TYPE: RNA
<213> ORGANISM: Artificial Sequence
<220> FEATURE:
<223> OTHER INFORMATION: synthetic primer/aptamer

<400> SEQUENCE: 111

```
gggagacaag aauaaacgcu caauaacggu agacauacgu gauaucuuca uaaccguacu    60
gcacgauucg acaggaggcu cacaacaggc                                    90
```

<210> SEQ ID NO 112
<211> LENGTH: 91
<212> TYPE: RNA
<213> ORGANISM: Artificial Sequence
<220> FEATURE:

<223> OTHER INFORMATION: synthetic primer/aptamer

<400> SEQUENCE: 112
gggagacaag aauaaacgcu caaugcauac ggugcauugu gcuccagccu cacacgaacg    60
auaagauuuc gacaggaggc ucacaacagg c                                  91

<210> SEQ ID NO 113
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 113
gggagacaag aauaaacgcu caaccguugu ucuacauguc acucaucaug cgagucuuuu    60
gucuaauuuc gacaggaggc ucacaacagg c                                  91

<210> SEQ ID NO 114
<211> LENGTH: 90
<212> TYPE: RNA
<213> ORGANISM: Artificial Sequence
<220> FEATURE:
<223> OTHER INFORMATION: synthetic primer/aptamer

<400> SEQUENCE: 114
gggagacaag aauaaacgcu caacucgugu gaccaacaua ccgcaugaau ugaccguucu    60
cauuaauucg acaggaggcu cacaacaggc                                    90

<210> SEQ ID NO 115
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 115
gggagacaag aauaaacgcu caaugccgug ccauuaacac gcaucgaaa uuugcugucg     60 uuacacauuc gacaggaggc ucacaacagg c                                  91

<210> SEQ ID NO 116
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 116
gggagacaag aauaaacgcu caauaccaaa cgcgcaauuu ucgucuugua auaaccaaau    60
gccucugauu cgacaggagg cucacaacag gc                                 92

<210> SEQ ID NO 117
<211> LENGTH: 90
<212> TYPE: RNA
<213> ORGANISM: Artificial Sequence
<220> FEATURE:
<223> OTHER INFORMATION: synthetic primer/aptamer

<400> SEQUENCE: 117
gggagacaag aauaaacgcu caaugauuuu gcagcacuuc uuguuaucuu aacgaacagu    60
ugaugauucg acaggaggcu cacaacaggc                                    90

<210> SEQ ID NO 118

```
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 118
gggagacaag aauaaacgcu caacuaccau gaccuuagcg cuuauugucu cgaccaucau    60
cacaauaauu cgacaggagg cucacaacag gc                                  92

<210> SEQ ID NO 119
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 119
gggagacaag aauaaacgcu caaaucaaac gcgucuugua aucauucucu cuaccuucac    60
aucguaauuc gacaggaggc ucacaacagg c                                   91

<210> SEQ ID NO 120
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 120
gggagacaag aauaaacgcu caaugcauac ggugcauugu gcuucagccu cacacgaacg    60
auaagauuuc gacaggaggc ucacaacagg c                                   91

<210> SEQ ID NO 121
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 121
gggagacaag aauaaacgcu caaacagcga uucgaucucu acccacaaca caaaugccuu    60
cacacauguu cgacaggagg cucacaacag gc                                  92

<210> SEQ ID NO 122
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 122
gggagacaag aauaaacgcu caacgugaac gucucaccaa ucggauagaa auugaucaag    60
ccuaguaauu cgacaggagg cucacaacag gc                                  92

<210> SEQ ID NO 123
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 123
gggagacaag aauaaacgcu caacgacacg uugccagccg gagccuuagu aacguacuuu    60
```

```
gaugucgauu cgacaggagg cucacaacag gc                                       92
```

<210> SEQ ID NO 124
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 124

```
gggagacaag aauaaacgcu caaucaucga uuucacaauu gagcuucgua ucagccucaa         60
caauuauuuu cgacaggagg cucacaacag gc                                       92
```

<210> SEQ ID NO 125
<211> LENGTH: 89
<212> TYPE: RNA
<213> ORGANISM: Artificial Sequence
<220> FEATURE:
<223> OTHER INFORMATION: synthetic primer/aptamer

<400> SEQUENCE: 125

```
gggagacaag aauaaacgcu caauguccau ucaacagauu cuuugucuua ccaaucagcc         60
uuuacuucga caggaggcuc acaacaggc                                           89
```

<210> SEQ ID NO 126
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 126

```
gggagacaag aauaaacgcu caaugauugc ggauucucau cuuuccaaca acgaacuagc         60
cucuacuauu cgacaggagg cucacaacag gc                                       92
```

<210> SEQ ID NO 127
<211> LENGTH: 91
<212> TYPE: RNA
<213> ORGANISM: Artificial Sequence
<220> FEATURE:
<223> OTHER INFORMATION: synthetic primer/aptamer

<400> SEQUENCE: 127

```
gggagacaag aauaaacgcu caaagaucga gugcuaaucu caacaacgaa aucuaugcgc         60
cucaauauuc gacaggaggc ucacaacagg c                                        91
```

<210> SEQ ID NO 128
<211> LENGTH: 92
<212> TYPE: RNA
<213> ORGANISM: Artificial Sequence
<220> FEATURE:
<223> OTHER INFORMATION: synthetic primer/aptamer

<400> SEQUENCE: 128

```
gggagacaag aauaaacgcu caacaacgaa gcuucuaugu cuuguucagc uuagccuguu         60
caacauaauu cgacaggagg cucacaacag gc                                       92
```

<210> SEQ ID NO 129
<211> LENGTH: 92
<212> TYPE: RNA
<213> ORGANISM: Artificial Sequence
<220> FEATURE:
<223> OTHER INFORMATION: synthetic primer/aptamer

```
<400> SEQUENCE: 129
gggagacaag aauaaacgcu caaaugcguc acacaaauug cucuuaacuu ugagccacug      60
caguaacauu cgacaggagg cucacaacag gc                                   92
```